United States Patent
Dohmen et al.

(10) Patent No.: US 11,020,487 B2
(45) Date of Patent: Jun. 1, 2021

(54) COMPOSITIONS FOR INTRODUCING NUCELIC ACID INTO CELLS (71) Applicant: ethris GmbH, Planegg (DE)

(72) Inventors: Christian Dohmen, Munich (DE); Christian Plank, Seefeld (DE); Carsten Rudolph, Krailing (DE)

(73) Assignee: ethris GmbH, Planegg (DE)

( * ) Notice: Subject to any disclaimer, the term of this patent is extended or adjusted under 35 U.S.C. 154(b) by 920 days.

(21) Appl. No.: 15/537,096

(22) PCT Filed: Dec. 18, 2015

(86) PCT No.: PCT/EP2015/080669
§ 371 (c)(1),
(2) Date: Jun. 16, 2017

(87) PCT Pub. No.: WO2016/097377
PCT Pub. Date: Jun. 23, 2016

(65) Prior Publication Data
US 2018/0236090 A1 Aug. 23, 2018

(30) Foreign Application Priority Data
Dec. 19, 2014 (EP) .................................. 14199439

(51) Int. Cl.
*A61K 47/59* (2017.01)
*A61K 48/00* (2006.01)
*C08G 73/02* (2006.01)
*C12N 15/87* (2006.01)

(52) U.S. Cl.
CPC .......... *A61K 47/59* (2017.08); *A61K 48/0041* (2013.01); *C08G 73/02* (2013.01); *C08G 73/0206* (2013.01); *C12N 15/87* (2013.01)

(58) Field of Classification Search
None
See application file for complete search history.

(56) References Cited

U.S. PATENT DOCUMENTS

| 5,656,611 A | 8/1997 | Kabanov et al. |
| 6,013,240 A | 1/2000 | Behr |
| 6,153,597 A | 11/2000 | Blanche |
| 2007/0269891 A9 | 11/2007 | Tanaka |

FOREIGN PATENT DOCUMENTS

| JP | S47 18664 | 6/1972 |
| JP | S58 21590 | 12/1983 |
| WO | WO 2001/005875 | 1/2001 |
| WO | WO 2007/120479 | 1/2001 |
| WO | WO 2014/025795 | 2/2014 |
| WO | WO 2014/152211 | 9/2014 |
| WO | WO2016/097377 A1 | 6/2016 |

OTHER PUBLICATIONS

Krämer, Michael. *Polymeric Nanocarriers with Dendritic Core-Shell Architectures.* Diss. 2004.
International Search Report in International Application No. PCT/EP2015/080669, dated Mar. 14, 2016.
Slonim, et al., "NMR spectroscopy of hetero-chain polymers," Moscow, "Khimiya" publishers, 1982, pp. 80-82.

*Primary Examiner* — Robert M Kelly
(74) *Attorney, Agent, or Firm* — Morse, Barnes-Brown & Pendleton, P.C.; Lisa M. Warren, Esq.

(57) ABSTRACT

The present invention relates to polymers comprising a characteristic combination of alkylene amine moieties which are useful as vehicles for transfecting a cell with a nucleic acid. The present invention furthermore relates to a composition comprising a nucleic acid and such a polymer, and to a method of transfecting a cell using said composition. Furthermore, the present invention relates to pharmaceutical compositions and uses.

15 Claims, 3 Drawing Sheets

COMPOSITIONS FOR INTRODUCING NUCELIC ACID INTO CELLS

CROSS-REFERENCE OF RELATED APPLICATIONS

This application is a United States National Stage under 35 U.S.C. § 371 of International Application No. PCT/EP2015/080669 (pending), filed Dec. 18, 2015, which claims the benefit of European Application No. 14199439.2, filed Dec. 19, 2014. The content of each of the aforementioned patent applications is hereby incorporated by reference in their entirety. International Application No. PCT/EP2015/080669 was published under PCT Article 21(2) in English.

The present invention relates to polymers comprising characteristic alkylene amine repeating units which are useful as vehicles for transfecting a cell with a nucleic acid, in particular RNA. The present invention furthermore relates to a composition comprising at least a nucleic acid and a polymer comprising such alkylene amine repeating units and to a method of transfecting a cell using said composition. Furthermore, the present invention relates to pharmaceutical compositions and uses.

The feasibility of nucleic acid therapies is ultimately dependent on the availability of efficient methods for delivering nucleic acids into cells.

In nucleic acid delivery in general, the use of naked nucleic acids is suitable and sufficient in some instances to transfect cells (Wolff et al. 1990, Science, 247, 1465-1468). However, in most envisaged practical applications it is advantageous or even necessary to formulate the nucleic acid with at least a second agent that protects the nucleic acid from degradation during delivery and/or facilitates distribution to and in a target tissue and/or facilitates cellular uptake and enables suitable intracellular processing. Such formulations for nucleic acid delivery are referred to as vectors in the scientific literature. A huge variety of compounds for the vectorization of nucleic acids, so-called transfection reagents, have been described previously. These compounds are usually either polycations or compositions comprising cationic lipids or lipid-like compounds such as lipidoids (U.S. Pat. No. 8,450,298). Complexes of nucleic acids with polycations are referred to as polyplexes, those with cationic lipids are referred to as lipoplexes (Feigner et al. 1997, Hum Gene Ther, 8, 511-512). Complexes comprising both a polycation and lipids have been described as well (Li and Huang in "Nonviral Vectors for Gene Therapy", Academic Press 1999, Chapter 13, 295-303). Transfection reagents are used to bind and compact nucleic acids to result in primary complexes in the nanometer size range. In salt-containing media these complexes tend to aggregate, also known as salt-induced aggregation, which can be advantageous for transfection in cell culture or localized administration in vivo (Ogris et al. 1998, Gene Ther, 5, 1425-1433; Ogris et al. 2001, AAPS PharmSci, 3, E21). Aggregation can be avoided and complexes of nucleic acids with transfection reagents can be stabilized by surface shielding with polymers such as poly(ethylene glycol). Shielding is also used to avoid opsonization of and complement activation by nucleic acid complexes with transfection reagents (Finsinger et al. 2000, Gene Ther, 7, 1183-1192). The compaction of nucleic acids by transfection reagents not only protects them against degradation by nucleases but also makes them suitable for cellular uptake by endocytosis. Numerous linear and branched polycations are suitable to bind and compact nucleic acids including but not limited to poly(ethylenimine), poly(amidoamine) dendrimers, poly(2-(dimethylamino)ethyl methacrylate) (pDMAEMA) or cationic derivatives of poly(N-(2-hydroxypropyl)methacrylamide) (pHPMA), poly(beta-amino ester)s (Akinc et al. 2003, Bioconj Chem 14(5):979-88), natural and synthetic cationic poly(amino acids) or peptides such as poly(lysines), histones, HMG proteins or cationic carbohydrates such as chitosans. Besides polymers containing primary-, secondary- and/or tertiary amines mentioned above structures containing guanidyl moieties are an important class of molecules for the purpose of nucleic acid complexation and delivery. Guanidyl modified polymers like arginine based structures (Yamanouchi et al. 2008, Biomaterials 29(22): 3269-77), PAMAM modified with arginine (Son et al. 2013, Bull. Korean Chem. Soc. Vol 34 No. 3) or guadinylated-PEI (Lee et al. 2008, Bull. Korean Chem. Soc. 2008, Vol. 29, No. 3) have highlighted the efficiency of such systems. Especially in case of RNA interaction, the molecular characteristics of the guanidyl moiety exhibits unique binding properties (Calnan et al. 19991, Science 252(5009), 1167-1171). For the generation of such structures methods as reviewed by Katritzky and Rogovoy (Katritzky & Rogovoy 2005, ARKIVOC (iv) 49-87) can be used. Often, polyplexes are further modified to contain a cell targeting or an intracellular targeting moiety and/or a membrane-destabilizing component such as an inactivated virus (Curiel et al. 1991, Proc-Natl Acad Sci USA, 88, 8850-8854), a viral capsid or a viral protein or peptide (Fender et al. 1997, Nat Biotechnol, 15, 52-56, Zhang et al. 1999, Gene Ther, 6, 171-181) or a membrane-disruptive synthetic peptide (Wagner et al. 1992, Proc Natl Acad Sci USA, 89, 7934-7938, Plank et al. 1994, J Biol Chem, 269, 12918-12924).

Upon endocytotic uptake, complexes are sequestered into intracellular vesicles such as endosomes and lysosomes where they are exposed to the cellular degradation machinery. Thus, it has been recognized that the escape from intracellular vesicles is essential for efficient functional nucleic acid delivery, a requirement that also applies for functional viral infection (Wagner et al. 1992, Proc Natl Acad Sci USA, 89, 7934-7938, Plank et al. 1994, J Biol Chem, 269, 12918-12924). The mechanisms that nature has evolved for viral infectivity have been mimicked to achieve efficient nucleic acid delivery by synthetic vectors. To this end, amphiphilic membrane-destabilizing peptides such as the INF, GALA and KALA peptides or melittin and melittin derivatives (Boeckle et al. 2006, J Control Release, 112, 240-248) have been used with great success to complement polycationic transfection reagents with endosomal escape functionality (Plank et al. 1998, Adv Drug Deliv Rev, 34, 21-35). In lipoplexes, such functionality is inherent by the ability of their lipid moieties to fuse with cellular membranes (Xu and Szoka 1996, Biochemistry, 35, 5616-5623, Zelphati and Szoka 1996, Proc Natl Acad Sci USA, 93, 11493-11498). Since the pivotal paper by Boussif et al. (Boussif et al. 1995, Proc Natl Acad Sci USA, 92, 7297-7301) it is known that the endosomal escape functionality of polyplexes can be realized by physico-chemical means. When poly(ethylenimine) (PEI) is used as a polycation to form polyplexes, its buffering capacity at acidic pH is sufficient to trigger endosomal escape. It is known that the lumen of endosomes is acidified by a proton pump residing in endosomal membranes (Lafourcade et al. 2008, PLoS One, 3, e2758). This acidification is the trigger for endosomal escape of some viruses such as influenza or adenovirus. The so-called proton sponge theory, supported by experimental evidence, describes the putative mechanistic action of polymers comprising chemical structural features of PEI: A substantial fraction of the aminogroups of PEI are un-protonated at neutral (physiological) pH (Ziebarth and Wang 2010, Biomacromolecules, 11, 29-38). By virtue of the protonated and thus positively charged aminogroups, PEI-like polymers can bind and compact nucleic acids. The unprotonated amines can become protonated at acidic pH, and thus have buffering capacity within endosomes. The endosomal acidification by the proton pump comes with accumulation of chloride ions (Sonawane et al. 2003, J Biol Chem, 278, 44826-44831). In the presence of a buffering molecule such as PEI in the endosomal lumen, the proton pump will shuttle way more protons into the endosomal lumen, along with chloride accumulation, as it would in its absence until the natural acidic endosomal pH is reached. The disproportionate accumulation of ions within the endosomes is thought to lead to an osmotic destabilization of the vesicles, leading ultimately to vesicle rupture and the release of the nucleic acid complex into the cytoplasm.

On the basis of the proton sponge theory, numerous researchers have picked up the structural features of PEI in creating novel polymer libraries comprising amines with buffering capacity at acidic pH. In U.S. Pat. No. 7,780,957 and U.S. Pat. No. 7,829,657 Kataoka et al. describe polymers based on a poly(glutamic acid) or poly(aspartic acid) backbone where the carboxylic acid side chains are derivatized with amine side chains protonatable at acidic pH. However, the rich structural space of oligo(alkylene amines) containing alternating, non-identical alkylene amine units to serve as transfection-enhancing moieties in polycations has not been explored. In particular, it has not been investigated previously for mRNA transfection.

In contrast, much of the scientific work of Kataoka et al. has focussed on poly{N-[N'-(2-aminoethyl)-2-aminoethyl] aspartamide}. In a publication by Uchida et al. (2011, J Am Chem Soc, 133, 15524-15532) the same group has examined a series of N-substituted polyaspartamides possessing repeating aminoethylene units in the side chains of the general formula —$(CH_2-CH_2-NH)_m$—H. Interestingly, when the authors examined the efficiency of the polymer family in transfection of plasmid DNA, "a distinctive odd-even effect of the repeating aminoethylene units in the polymer side chain on the efficiencies of endosomal escape and transfection to several cell lines was observed. The polyplexes from the polymers with an even number of repeating aminoethylene units (PA-Es) achieved an order of magnitude higher transfection efficiency, without marked cytotoxicity, than those of the polymers with an odd number of repeating aminoethylene units (PA-Os). This odd-even effect agreed well with the buffering capacity of these polymers as well as their capability to disrupt membrane integrity selectively at endosomal pH, leading to highly effective endosomal escape of the PA-E polyplexes. Furthermore, the formation of a polyvalent charged array with precise spacing between protonated amino groups in the polymer side chain was shown to be essential for effective disruption of the endosomal membrane, thus facilitating transport of the polyplex into the cytoplasm" (Abstract from Uchida et al. 2011, J Am Chem Soc, 133, 15524-15532). Interestingly, when the same group of researchers compared poly(aspartamide) derivatives bearing 1,2-diaminoethane side chains, [PAsp(DET)] versus analogues bearing 1,3-diaminopropane side chains, [PAsp(DPT)], they observed that PAsp(DPT) polyplexes showed a significant drop in the transfection efficacy of plasmid DNA at high N/P ratios due to the progressively increased cytotoxicity with N/P ratio, even though the physicochemical differences to [PAsp(DET)] in particle size and ζ-potential were negligible (Miyata et al. 2008, J Am Chem Soc, 130, 16287-16294). Hence, based on the odd-even rule one would expect that polymers comprising 3 protonatable amino groups and propylene spacer groups would be inferior to PAsp(DET) and that 1,3-diaminopropane-comprising side chains are associated with toxicity problems. Nothing is known about structure-activity relationships of such polymers for mRNA transfection.

M. Krämer, "Polymeric Nanocarriers with Dendritic Core-Shell Architectures", Dissertation, Albert-Ludwigs-Universität Freiburg i.Br., 2004, describes gene transfection using particles of PEI based dendrimers which may be grafted with propyleneimine side chains or end groups.

Geall and colleagues have described cholesterol-polyamine carbamates with the polyamine moiety having the general formula:

where m=0, 1 or 2 and where n=0 or 1 (Geall et al. 1999, FEBS Lett, 459, 337-342). They have examined the $pK_a$ values of these substances and their characteristics in condensation of calf thymus DNA. They found that the regiochemical distribution of positive charges along cholesterol polyamine carbamates plays significant roles in modulating DNA binding affinity and lipofection efficiency. They found that among the examined cholesterol-polyamine carbamates, spermine constituting the polyamine moiety, —HN—$CH_2$—$CH_2$—$CH_2$—NH—$CH_2$—$CH_2$—$CH_2$—$CH_2$—NH—$CH_2$—$CH_2$—$CH_2$—$NH_2$ (propyl/butyl/propyl) yielded by far the highest reporter gene expression upon transfection of beta galactosidase-encoding plasmid DNA in cell culture, while for example —HN—$CH_2$—$CH_2$—NH—$CH_2$—$CH_2$—$CH_2$—NH—$CH_2$—$CH_2$—$NH_2$ (ethyl/propyl/ethyl) was three- to tenfold less efficient. Hence, in view of the teachings of Kataoka et al. (odd-even rule) and the findings of Geall et al. the one skilled in the art would dismiss the latter structure in the context of nucleic acid delivery.

Wang et al. have described poly(methyl methacrylate)-graft-oligoamines as efficient and low cytotoxic transfection reagents for plasmid DNA (Wang et al. 2010, Molecular BioSystems, 6, 256-263). These polymers were obtained by aminolysis of poly(methyl methacrylate) with oligoamines of the general formula $H_2N$—$CH_2$—$CH_2$—(NH—$CH_2$—$CH_2)_m$—$NH_2$, where m=1, 2, or 3. The authors found that transfection efficiency increased with an increasing length of amines.

Ou et al. have described poly(disulphide amido amines) which are derived from terminally protected oligo amines having the structure Dde-NH—$(CH_2)_a$—NH—$(CH_2)_b$—NH—$(CH_2)_a$—NH-Dde by co-polymerization with N,N'-cystaminebisacrylamide (Ou et al. 2009, Biomaterials 30, 5804-5814; WO 2010/065660). They examined the combinations a=2 and b=2, a=2 and b=3, a=3 and b=2, a=3 and b=3, a=3 and b=4 (spermine). Dde is the 2-acetyldimedone protecting group. After removal of the protecting group, the synthesis yields poly(disulphide amido amines) where the internal, originally secondary amines become tertiary amines as part of the polymer main chain and the terminal amines become part of pending ethylene or propylene amine side chains. Such polymers have buffering capacity in the pH range relevant for nucleic acid delivery and are useful for transfecting plasmid DNA into cells.

Recently, the utility of a new class of lipid-like but non-lipidic synthetic structures, so-called lipidoids, for nucleic acid delivery in vitro and in vivo has been discovered (U.S. Pat. No. 8,450,298; Love et al. 2010, PNAS 107, 1864-1869; WO2006/138380; Akinc et al. 2008, Nat Biotechnol 26, 561-569). Lipidoids are obtained by reacting amine-containing compounds with aliphatic epoxides, acrylates, acrylamides or aldehydes. The authors/inventors have provided synthetic procedures for obtaining lipidoid libraries and screening procedures for selecting useful compounds with utility in nucleic acid delivery to cells in vitro.

As is evident from the above, much research and development work has been done in the past on the delivery of other nucleic acid molecules such as plasmid DNA, oligonucleotides, siRNA or nucleic acid analogues. mRNA delivery has not been investigated in much depth. Some authors have alleged that compounds and formulations which work well for DNA or siRNA delivery would work alike for mRNA delivery. However, in contrast to plasmid DNA or siRNA, mRNA is a single-stranded molecule. Hence, based just on structural considerations one would expect different requirements for compounds and formulations for mRNA delivery versus DNA or siRNA delivery.

The previous literature cited above describes the delivery of double-stranded nucleic acids such as plasmid DNA or siRNA into cells but it is not known whether the described methods and compounds are capable of delivering single stranded nucleic acids such as mRNA into cells. Notably, it has been observed previously that mRNA transfection differs substantially from plasmid DNA transfection into cells (Bettinger et al. 2001, Nucleic Acids Res, 29,3882-91, Uzgün et al, 2011, Pharm Res, 28, 2223-32).

In line with this, the present inventors found that, when screening more than 100 members of a polymer family disclosed in WO 2011/154331 for their suitability in RNA delivery, preferably delivery of single-stranded RNA such as mRNA, to cells, none of the compounds was useful to transfect mRNA in a manner giving rise to the expression of a gene encoded by the mRNA. In contrast, all these compounds are efficient in plasmid DNA and/or siRNA delivery. Hence, the established rules for delivery of double-stranded nucleic acids into cells do not apply a priori for single stranded mRNA. The disclosure of WO 2011/154331 comprises chemically defined oligomers being 2-60 units of oligo(alkylene amino) acid units which correspond to the general formula HOOC—Z—R—NH—[(CH$_2$)$_b$—NH]$_a$—H, where Z is a series of methylene or a variety of other groupings, R is a methylene or carboxy residue and a and b are independently integers of 1-7 or 2-7, respectively. Oligomers of this family comprise protonatable amino groups able to exert a so called proton sponge effect and have been shown to be highly active in the transfection of plasmid DNA and siRNA in vitro and in vivo. Importantly, WO 2011/154331 and associated scientific publications teach in great detail how sequence-defined oligomer/polymer libraries can be established from building blocks corresponding to the general formula HOOC—Z—R—NH—[(CH$_2$)$_b$—NH]$_a$—H.

The technical task underlying the present invention thus was to provide a composition that is suitable for delivery of nucleic acids, and in particular RNA, preferably single stranded-RNA such as mRNA, with a high efficiency into a cell or to a tissue.

This task has been accomplished by the provision of the embodiments as characterized in the claims and illustrated in further detail in the following general description and the examples.

It was surprisingly found that copolymers containing a statistical/random arrangement of alkylene amine repeating units of alternating length in compositions for transfecting a cell with a nucleic acid, in particular RNA, preferably a single-stranded RNA such as mRNA, was consistently more efficacious than polymers containing analogous arrangements of alkylene amine repeating units of non-alternating length.

Thus, the invention provides, in a first aspect, a statistical copolymer comprising a plurality of repeating units (a) independently selected from repeating units of the following formulae (a1) and (a2):

and a plurality of repeating units (b) independently selected from repeating units of the following formulae (b1) to (b4):

wherein the molar ratio of the sum of the repeating units (a) to the sum of the repeating units (b) lies within the range of 0.7/1.0 to 1.0/0.7, and wherein one or more of the nitrogen atoms of the repeating units (a) and/or (b) contained in the copolymer may be protonated to provide a cationic copolymer.

In a further aspect, the invention provides a composition comprising a nucleic acid, in particular an RNA, preferably a single-stranded RNA such as mRNA, and the above copolymer.

In further aspects, the invention relates pharmaceutical compositions comprising the compositions in accordance with the invention. The invention also encompasses methods for the preparation of the copolymers in accordance with the invention as well as the compositions and pharmaceutical compositions in accordance with the invention.

Still further aspects are directed to the use of a composition in accordance with the invention or a copolymer in accordance with the invention for delivering a nucleic acid, in particular RNA, preferably a single-stranded RNA such as mRNA, into a target cell or to tissue, and to a method for delivering a nucleic acid, in particular RNA, preferably single-stranded RNA such as mRNA, into a cell comprising the step of bringing a composition in accordance with the invention into contact with the cell.

The copolymers in accordance with the present invention combine shorter repeating units (a) with longer repeating units (b) in the form of a statistical copolymer, in particular a random copolymer, and in defined ratios. This arrangement of the repeating units (a) and (b) has been found to provide unexpected advantages in terms of the suitability of the resulting copolymer as a vehicle for delivering a nucleic acid, in particular an RNA, preferably a single-stranded RNA such as mRNA, into a cell.

As noted above, the copolymer in accordance with the invention is a statistical copolymer comprising a plurality of repeating units (a) independently selected from repeating units of the following formulae (a1) and (a2):

(a1)

(a2)

and a plurality of repeating units (b) independently selected from repeating units of the following formulae (b1) to (b4):

(b1)

(b2)

(b3)

(b4)

wherein the molar ratio of the sum of the repeating units (a) to the sum of the repeating units (b) lies within the range of 0.7/1.0 to 1.0/0.7, and wherein one or more of the nitrogen atoms of the repeating units (a) and/or (b) contained in the copolymer may be protonated to provide a cationic copolymer.

The copolymer is a statistical copolymer, wherein any repeating units (a) and any repeating units (b) are statistically distributed in the copolymer macromolecule. It is typically obtained from the copolymerization of a mixture of monomers yielding, during the polymerization reaction, the repeating units (a) with monomers yielding, during the polymerization reaction, the repeating units (b). Preferably, the copolymer is a random copolymer wherein any repeating units (a) and any repeating units (b) are randomly distributed in the polymer macromolecule.

The copolymer in accordance with the invention can be a linear, branched or dendritic copolymer. As will be understood by the skilled reader, a repeating unit of the formula (a1), (b1) or (b3) with two valencies (i.e. open bonds to neighboring units) leads to a propagation of the copolymer structure in a linear manner. Thus, a linear copolymer of the invention comprises repeating units of formula (a1) and one or more types of the repeating units of formulae (b1) and (b3), but no repeating units of formula (a2), (b2) or (b4). As will be further understood, the presence of a repeating unit of formula (a2), (b2) or (b4) with three valencies provides a branching point in the copolymer structure. Thus, a branched copolymer comprises one or more types of the repeating units of formulae (a2), (b2) and (b4), and may further comprise one or more types of the repeating units of formulae (a1), (b1) and (b3).

The copolymer in accordance with the invention comprises a plurality of repeating units (a) independently selected from repeating units of formulae (a1) and (a2) defined above, and a plurality of repeating units (b) independently selected from repeating units of formulae (b1) to (b4) defined above. Preferred are copolymers comprising a plurality of repeating units (a) independently selected from repeating units of formulae (a1) and (a2) defined above, and a plurality of repeating units (b) independently selected from repeating units of formulae (b1) and (b2) defined above.

It is also preferred that the copolymer in accordance with the invention is a branched copolymer comprising one or more types of repeating units selected from repeating units (a2), (b2) and (b4), and which optionally further comprises one or more types of the repeating units of formulae (a1), (b1) and (b3), and in particular a copolymer which comprises repeating units of the formula (a2) and one or more type of the repeating units of formulae (b2) and (b4), and which optionally further comprises one or more types of the repeating units of formulae (a1), (b1) and (b3). In line with the above, a more preferred copolymer is thus a branched copolymer which comprises repeating units of the formula (a2) and repeating units of formula (b2), and which optionally further comprises one or more types of the repeating units of formulae (a1) and (b1).

In the copolymers in accordance with the invention, the total number of the repeating units (a) and repeating units (b) is typically 20 or more, preferably 50 or more and more preferably 100 or more. Typically, the total number of the repeating units (a) and repeating units (b) is 5,000 or less, preferably 2,500 or less, more preferably 1,000 or less and in particular 500 or less.

Furthermore, it is preferred for the copolymers in accordance with the invention that the repeating units (a) and (b) account for 80 mol % or more, more preferably 90 mol % or more of all repeating units in the copolymer. Further preferred are copolymers wherein repeating units (a) selected from (a1) and (a2) and repeating units (b) selected from (b1) and (b2) account for 80 mol % or more, more preferably 90 mol % or more of all repeating units in the copolymer. It is most preferred that all of the repeating units in the copolymer are repeating units (a) or (b), in particular that all of the repeating units in the copolymer are repeating units (a) selected from (a1) and (a2) or repeating units (b) selected from (b1) and (b2).

The weight average molecular weight of the copolymer in accordance with the present invention, as measured e.g. via size exclusion chromatography relative to linear poly(ethylene oxide) standards, generally ranges from 1,000 to 500,000 Da, preferably from 2,000 to 250,000 Da and more preferably 5,000-50,000 Da.

The terminal groups of the copolymer in accordance with the invention typically comprise one or more types of groups (c) independently selected from groups of the formulae (c1) to (c3) below, preferably from groups of the formulae (c1) and (c2) below:

(c1)

(c2)

(c3).

Preferably, the terminal groups in the copolymer consist of one or more types of groups (c) independently selected from groups of the formulae (c1) to (c3) below, preferably from groups of the formulae (c1) and (c2). As will be understood by the skilled person, the number of terminal groups depends on the structure of the copolymer in accordance with the invention. While a linear copolymer has only two terminals, larger numbers of terminal groups are contained in a branched, in particular in a dendritic copolymer. As will be further understood, also one or more of the nitrogen atoms of the terminal groups (c) contained in the copolymer may be protonated to provide a cationic copolymer.

In the copolymer in accordance with the invention, the molar ratio of the sum of the repeating units (a) to the sum of the repeating units (b) lies within the range of 0.7/1.0 to 1.0/0.7, and preferably within the range of 0.8/1.0 to 1.0/0.8. This molar ratio can be determined, e.g., via NMR. It will thus be understood that the ratio is usually determined for a plurality of macromolecules of the copolymer in accordance with the invention, and typically indicates the overall ratio of the sum of repeating units (a) to the sum of repeating units (b) in the plurality of macromolecules.

As indicated above, one or more of the nitrogen atoms of the copolymer in accordance with the invention may be protonated to result in a copolymer in a cationic form, typically an oligocationic or polycationic form. It will be understood that the primary, secondary, or tertiary amino groups in the repeating units (a) or (b) or in the terminal groups (c) can act as proton acceptors, especially in water and aqueous solutions, including physiological fluids. Thus, the copolymers of the present invention typically have an overall positive charge in an aqueous solution at a pH of below 7.5. An aqueous solution, as referred to herein, is a solution wherein the solvent comprises 50% (vol./vol.) or more, preferably 80 or 90% or more, and most preferably 100% of water. Also, if the compositions in accordance with the invention are in contact with a physiological fluid having a pH of below 7.5, including e.g. blood and lung fluid, they typically contain repeating units (a) and (b) wherein the nitrogen atoms are protonated. The $pK_a$ values of the copolymers used in the compositions in accordance with the invention can be determined by acid-base titration using an automated $pK_a$ titrator. The net charge at a given pH value can then be calculated e.g. from the Henderson-Hasselbach equation. Any charge may be shared across several of the basic centres and cannot necessarily be attributed to a single point. Typically, in solutions at physiological pH, the copolymers used in the compositions in accordance with the invention comprise repeating units with amino groups in protonated state and repeating units with amino groups in unprotonated state.

However, as will be understood by the skilled reader, the copolymers in accordance with the invention as well as the compositions in accordance with the invention may also be provided as a dry salt form which contains the copolymer in a cationic form.

As will be further understood, counterions (anions) for the positive charges of protonated amino groups in compositions according to the invention comprising the copolymer and nucleic acid, in particular RNA, preferably single-stranded RNA such as mRNA, are typically provided by anionic moieties contained in the nucleic acid. If the positively charged groups are present in excess compared to the anionic moieties in the nucleic acid, positive charges may be balanced by other anions, in particular those typically encountered in physiological fluids, such as $Cl^-$ or $HCO_3^-$.

In line with the above, a preferred copolymer in accordance with the invention is a random copolymer, wherein
80 mol % or more of all repeating units, more preferably all repeating units, are formed by
a plurality of repeating units (a) independently selected from repeating units of the following formulae (a1) and (a2):

(a1)

(a2)

and
a plurality of repeating units (b) independently selected from repeating units of the following formulae (b1) and (b2):

(b1)

(b2)

wherein the molar ratio of the sum of the repeating units (a) to the sum of the repeating units (b) lies within the range of 0.7/1.0 to 1.0/0.7, more preferably within the range of 0.8/1.0 to 1.0/0.8;
wherein the terminal groups of the copolymer are formed by groups (c) independently selected from groups of the formulae (c1) and (c2):

(c1)

(c2); and wherein one or more of the nitrogen atoms of the repeating units (a) and/or (b) and/or of the terminal groups (c) contained in the copolymer may be protonated to provide a cationic copolymer. It is further preferred that the copolymer is a branched copolymer, comprising units (a2) and (b2), optionally together with units (a1) and/or (b1).

The copolymers in accordance with the invention can be conveniently prepared with procedures analogous to those known for the preparation of polyalkyleneimines, such as branched or linear polyethyleneimine (PEI). It will be understood that the monomers used for the production of the copolymers will have to be adjusted accordingly. In the context of the present invention, it has been found that the monomers can be conveniently reacted in a quantitative manner, such that the ratio of the units (a) and (b) in the copolymer can be adjusted by adjusting the monomer ratio accordingly in the monomer mixture subjected to polymerization. While polyethyleneimine, also referred to as polyaziridine, can be prepared e.g. via ring-opening polymerization of aziridine, the copolymers in accordance with the invention can be prepared via ring opening polymerization of a monomer mixture comprising or consisting of aziridine, azetidine and, where applicable pyrrolidine, or, in preferred embodiments, of aziridine and azetidine. It will be understood that the expression "where applicable" refers to the presence or absence of repeating units (b3) and (b4) or terminal groups (c3) which would be formed by the pyrrolidine. The ring opening polymerization of the non-substituted cyclic amines usually leads to branched copolymers. Linear copolymers in accordance with the invention can be prepared, e.g., via polymerization of suitable N-substituted aziridines, N-substituted azetidines and N-substituted pyrrolidines, or N-substituted aziridines and N-substituted azetidines, which may be followed e.g. by a hydrolytic cleavage of N-substituents attached to the resulting polyalkyleneimine chain, e.g. in analogy to the procedure published in Katrien F. Weyts, Eric J. Goethals, New synthesis of linear polyethyleneimine, Polymer Bulletin, January 1988, Volume 19, Issue 1, pp 13-19.

For the preparation of a dendrimer (or dendritic copolymer), synthetic strategies can be analogously applied which are known for the production of polyethyleneimine or polypropyleneamine dendrimers. Polypropylenimine dendrimers can be synthesized from acrylonitrile building blocks using a repetitive sequence of a Michael addition to a primary amine, followed by a heterogeneously catalyzed hydrogenation (Newkome and Shreiner Poly(amidoamine), polypropylenimine, and related dendrimers and dendrons possessing different 1→2 branching motifs: An overview of the divergent procedures. Polymer 49 (2008) 1-173; De Brabander-Van Den Berg et al. Large-scale production of polypropylenimine dendrimers, Macromolecular Symposia (1994) 77 (1) 51-62). Polyethylenimine dendrimers can be produced using a repetitive sequence of a Michael addition of a vinyl bromide building block to a primary amine followed by a conversion of alkylbromide to amine using a Gabriel amine synthesis method (Yemul & lmae, Synthesis and characterization of poly(ethyleneimine) dendrimers, Colloid Polym Sci (2008) 286:747-752). Hence the person skilled in the art will be able to produce not only dendrimers with strictly alternating layers of e.g. propylenimine and ethylenimine can be produced. Similarly dendrimer generations with layers comprising or consisting of random compositions of repeating units of formula (a2), (b2) and (b4) and preferably repeating units (a2) and (b2) can be generated.

The ring opening polymerization of aziridine and azetidine, or of aziridine, azetidine and pyrrolidine, can be carried out in solution, e.g. in water. The total monomer concentration is not particularly limited, typical concentrations range from 10% wt/wt to 80% wt/wt, preferably 30% wt/wt to 60% wt/wt. Typically, the polymerization is initiated by protons, such that it is preferred to add a Brønsted acid, in particular a mineral acid such as sulphuric acid to the reaction system. Small amounts of acid are generally sufficient, such as 0.001 to 0.01 equivalents, based on the total concentration of monomers. The reaction proceeds at convenient rates e.g. in the temperature range of 50 to 150° C., in particular 90 to 140° C. In these ranges, higher molecular weight copolymers are usually at higher temperatures, and lower molecular weight copolymers at lower temperatures.

Nucleic Acid

As noted above, a central aspect of the invention is a composition comprising a nucleic acid, in particular an RNA, preferably a single-stranded RNA such as mRNA, and the above copolymer in accordance with the invention.

The term "nucleic acid" encompasses all forms of naturally occurring types of nucleic acids as well as chemically and/or enzymatically synthesized nucleic acids and also encompasses nucleic acid analogues and nucleic acid derivatives such as e.g. locked nucleic acids (LNA), peptide nucleic acids (PNA), oligonucleoside thiophosphates and phosphotriesters, morpholino oligonucleotides, cationic oligonucleotides (U.S. Pat. No. 6,017,700 A, WO/2007/069092), substituted ribo-oligonucleotides or phosphorothioates. Furthermore, the term "nucleic acid" also refers to any molecule that comprises nucleotides or nucleotide analogues. There are no limitations concerning sequence or size of a nucleic acid comprised in the composition of the present invention. The nucleic acid is predominantly defined by the biological effect that is to be achieved at the biological target the composition of the present invention is delivered to. For instance, in the case of an application in gene or nucleic acid therapy, the nucleic acid or nucleic acid sequence can be defined by the gene or gene fragment that is to be expressed or by the intended substitution or repair of a defective gene or any gene target sequence or by the target sequence of a gene to be inhibited, knocked-down or down-regulated.

Preferably, the term "nucleic acid" refers to oligonucleotides or polynucleotides, including deoxyribonucleic acid (DNA) and ribonucleic acid (RNA). As regards RNA, in principle any type of RNA can be employed in the context of the present invention. In one preferred embodiment the RNA is a single-stranded RNA. The term "single-stranded RNA" means a single consecutive chain of ribonucleotides in contrast to RNA molecules in which two or more separate chains form a double-stranded molecule due to hybridization of the separate chains. The term "single-stranded RNA" does not exclude that the single-stranded molecule forms in itself double-stranded structures such as loops, secondary or tertiary structures.

The term "RNA" covers RNA which codes for an amino acid sequence as well as RNA which does not code for an amino acid sequence. It has been suggested that more than 80% of the genome contains functional DNA elements that do not code for proteins. These noncoding sequences include regulatory DNA elements (binding sites for transcription factors, regulators and coregulators etc.) and sequences that code for transcripts that are never translated into proteins. These transcripts, which are encoded by the genome and transcribed into RNA but do not get translated into proteins, are called noncoding RNAs (ncRNAs). Thus, in one embodiment the RNA is a noncoding RNA. Preferably, the noncoding RNA is a single-stranded molecule. Studies demonstrate that ncRNAs are critical players in gene regulation, maintenance of genomic integrity, cell differentiation, and development, and they are misregulated in various human diseases. There are different types of ncRNAs: short (20-50 nt), medium (50-200 nt), and long (>200 nt) ncRNAs. Short ncRNA includes microRNA (miRNA), small interfering RNA (siRNA), piwi-interacting RNA (piRNA), and transcription initiating RNA (tiRNA). Examples of medium ncRNAs are small nuclear RNAs (snRNAs), small nucleolar RNAs (snoRNAs), transfer RNAs (tRNAs), transcription start-site-associated RNAs (TSSaRNAs), promoter-associated small RNAs (PASRs), and promoter upstream transcripts (PROMPTs). Long noncoding RNAs (lncRNA) include long-intergenic noncoding RNA (lincRNA), antisense-lncRNA, intronic lncRNA, transcribed ultra-conserved RNAs (T-UCRs), and others (Bhan A, Mandal S S, ChemMedChem. 2014 Mar. 26. doi: 10.1002/cmdc.201300534). Of the above-mentioned non-coding RNAs only siRNA is double-stranded. Thus, since in a preferred embodiment the noncoding RNA is single-stranded, it is preferred that the noncoding RNA is not siRNA. In another embodiment the RNA is a coding RNA, i.e. an RNA which codes for an amino acid sequence. Such RNA molecules are also referred to as mRNA (messenger RNA) and are single-stranded RNA molecules. The nucleic acids may be made by synthetic chemical and enzymatic methodology known to one of ordinary skill in the art, or by the use of recombinant technology, or may be isolated from natural sources, or by a combination thereof. The oligo- or polynucleotides may optionally comprise unnatural nucleotides and may be single or double or triple stranded. "Nucleic acid" also refers to sense and anti-sense oligo- or polynucleotides, that is, a nucleotide sequence which is complementary to a specific nucleotide sequence in a DNA and/or RNA.

Preferably, the term nucleic acid in the context of the present invention refers to RNA, more preferably to single stranded RNA, in particular to mRNA and most preferably to modified mRNA.

Messenger RNAs (mRNA) are copolymers which are built up of nucleoside phosphate building blocks mainly with adenosine, cytidine, uridine and guanosine as nucleosides, which as intermediate carriers bring the genetic information from the DNA in the cell nucleus into the cytoplasm, where it is translated into proteins. They are thus suitable as alternatives for gene expression.

In the context of the present invention, mRNA should be understood to mean any polyribonucleotide molecule which, if it comes into the cell, is suitable for the expression of a protein or fragment thereof or is translatable to a protein or fragment thereof. The term "protein" here encompasses any kind of amino acid sequence, i.e. chains of two or more amino acids which are each linked via peptide bonds and also includes peptides and fusion proteins.

The mRNA contains a ribonucleotide sequence which encodes a protein or fragment thereof whose function in the cell or in the vicinity of the cell is needed or beneficial, e.g. a protein the lack or defective form of which is a trigger for a disease or an illness, the provision of which can moderate or prevent a disease or an illness, or a protein which can promote a process which is beneficial for the body, in a cell or its vicinity. The mRNA may contain the sequence for the complete protein or a functional variant thereof. Further, the ribonucleotide sequence can encode a protein which acts as a factor, inducer, regulator, stimulator or enzyme, or a functional fragment thereof, where this protein is one whose function is necessary in order to remedy a disorder, in particular a metabolic disorder or in order to initiate processes in vivo such as the formation of new blood vessels, tissues, etc. Here, functional variant is understood to mean a fragment which in the cell can undertake the function of the protein whose function in the cell is needed or the lack or defective form whereof is pathogenic. In addition, the mRNA may also have further functional regions and/or 3' or 5' noncoding regions. The 3' and/or 5' noncoding regions can be the regions naturally flanking the protein-encoding sequence or artificial sequences which contribute to the stabilization of the RNA. Those skilled in the art can determine the sequences suitable for this in each case by routine experiments.

In a preferred embodiment, the mRNA contains an m7GpppG cap, an internal ribosome entry site (IRES) and/or a polyA tail at the 3' end in particular in order to improve translation. The mRNA can have further regions promoting translation.

In a preferred embodiment the mRNA is an mRNA which contains a combination of modified and unmodified nucleotides. Preferably, it is an mRNA containing a combination of modified and unmodified nucleotides as described in WO2011/012316. The mRNA described therein is reported to show an increased stability and diminished immunogenicity. In a preferred embodiment, in such a modified mRNA 5 to 50% of the cytidine nucleotides and 5 to 50% of the uridine nucleotides are modified. The adenosine- and guanosine-containing nucleotides can be unmodified. The adenosine and guanosine nucleotides can be unmodified or partially modified, and they are preferably present in unmodified form. Preferably 10 to 35% of the cytidine and uridine nucleotides are modified and particularly preferably the content of the modified cytidine nucleotides lies in a range from 7.5 to 25% and the content of the modified uridine nucleotides in a range from 7.5 to 25%. It has been found that in fact a relatively low content, e.g. only 10% each, of modified cytidine and uridine nucleotides can achieve the desired properties. It is particularly preferred that the modified cytidine nucleotides are 5-methylcytidin residues and the modified uridine nucleotides are 2-thiouridin residues. Most preferably, the content of modified cytidine nucleotides and the content of the modified uridine nucleotides is 25%, respectively.

In another preferred embodiment, the mRNA may be combined with target binding sites, targeting sequences and/or with micro-RNA binding sites, in order to allow activity of the desired mRNA only in the relevant cells. In a further preferred embodiment, the RNA can be combined with micro-RNAs or shRNAs downstream of the 3' polyA tail.

Furthermore, the term "nucleic acid(s)" may refer to DNA or RNA or hybrids thereof or any modification thereof that is known in the state of the art (see, e.g., U.S. Pat. No. 8,278,036, WO 2013/052523, WO 2011/012316, U.S. Pat. No. 5,525,711, U.S. Pat. No. 4,711,955, U.S. Pat. No. 5,792,608 or EP 302175, (Lorenz et al. 2004, Bioorg Med Chem Lett, 14, 4975-4977; Soutschek et al. 2004, Nature, 432, 173-178) for examples of modifications). Such nucleic acid molecule(s) are single- or double-stranded, linear or circular, natural or synthetic, and without any size limitation. For instance, the nucleic acid molecule(s) may be genomic DNA, cDNA, mRNA, antisense RNA, ribozyme, or small interfering RNAs (siRNAs), micro RNAs, antagomirs, or short hairpin RNAs (shRNAs), tRNAs or long double-stranded RNAs or a DNA construct encoding such RNAs or chimeraplasts (Colestrauss et al. 1996, Science, 273, 1386-1389), or aptamers, clustered regularly interspaced short palindromic repeats ("CRISPR" for RNA-guided site-specific DNA cleavage) (Cong et al. 2013, Science, 339, 819-823), or RNA and DNA. Said nucleic acid molecule(s) may be in the form of plasmids, cosmids, artificial chromosomes, viral DNA or RNA, bacteriophage DNA, coding and non-coding single-stranded (mRNA) or double-stranded RNA and oligonucleotide(s), wherein any of the state of the art modifications in the sugar backbone and/or in the bases as described above and 3'- or 5'-modifications are included. In a particularly preferred embodiment the nucleic acid is RNA, more preferably mRNA or siRNA.

The nucleic acid(s) may contain a nucleotide sequence encoding a polypeptide that is to be expressed in a target cell. Methods which are well known to those skilled in the art can be used to construct recombinant nucleic acid molecules; see, for example, the techniques described in Sambrook et al., Molecular Cloning A Laboratory Manual, Cold Spring Harbor Laboratory (2001) N.Y. and Ausubel et al., Current Protocols in Molecular Biology, Green Publishing Associates and Wiley Interscience, N.Y. (1989).

In a preferred embodiment, said nucleic acid is a therapeutically or pharmaceutically active nucleic acid including all nucleic acid types and modifications listed above and those known to the one skilled in the art which may have a therapeutic or preventive effect. In general, therapeutic or preventive effects can be achieved by the interaction of the nucleic acid with cellular molecules and organelles. Such interaction alone may for example activate the innate immune system, as is the case for certain CpG oligonucleotides and sequences designed to specifically interact with toll-like and other extra- or intracellular receptors. Furthermore, the uptake or introduction of nucleic acids in cells can be intended to lead to the expression of nucleotide sequences such as genes comprised in the nucleic acid, can be intended for the downregulation, silencing or knockdown of endogenous gene expression as a consequence of the intracellular presence of an introduced exogenous nucleic acid, or can be intended for the modification of endogenous nucleic acid sequences such as repair, excision, insertion or exchange of selected bases or of whole stretches of endogenous nucleic acid sequences, or can be intended for interference with virtually any cellular process as a consequence of the intracellular presence and interaction of an introduced exogenous nucleic acid. Overexpression of introduced exogenous nucleic acids may be intended to compensate or complement endogenous gene expression, in particular in cases where an endogenous gene is defective or silent, leading to no, insufficient or a defective or a dysfunctional product of gene expression such as is the case with many metabolic and hereditary diseases like cystic fibrosis, hemophilia or muscular dystrophy to name a few. Overexpression of introduced exogenous nucleic acids may also be intended to have the product of the expression interact or interfere with any endogenous cellular process such as the regulation of gene expression, signal transduction and other cellular processes. The overexpression of introduced exogenous nucleic acids may also be intended to give rise to an immune response in context of the organism in which a transfected or transduced cell resides or is made to reside. Examples are the genetic modification of antigen-presenting cells such as dendritic cells in order to have them present an antigen for vaccination purposes. Other examples are the overexpression of cytokines in tumors in order to elicit a tumor-specific immune response. Furthermore, the overexpression of introduced exogenous nucleic acids may also be intended to generate in vivo or ex vivo transiently genetically modified cells for cellular therapies such as modified T-cells or precursor or stem or other cells for regenerative medicine.

Downregulation, silencing or knockdown of endogenous gene expression for therapeutic purposes can for example be achieved by RNA interference (RNAi), with ribozymes, antisense oligonucleotides, tRNAs, long double-stranded RNA where such downregulation can be sequence-specific or unspecific and can also lead to cell death as is the case when long double-stranded RNAs are introduced into cells. Downregulation, silencing or knockdown of endogenous or pre-existing gene expression can be useful in the treatment of acquired, hereditary or spontaneously incurring diseases including viral infections and cancer. It can also be envisaged that the introduction of nucleic acids into cells can be practiced as a preventive measure in order to prevent, for example, viral infection or neoplasias. Downregulation, silencing or knockdown of endogenous gene expression can be exerted on the transcriptional level and on the translational level. Multiple mechanisms are known to the one skilled in the art and include for example epigenetic modifications, changes in chromatin structure, selective binding of transcription factors by the introduced nucleic acid, hybridization of the introduced nucleic acid to complementary sequences in genomic DNA, mRNA or other RNA species by base pairing including unconventional base pairing mechanisms such as triple helix formation. Similarly, gene repair, base or sequence changes can be achieved at the genomic level and at the mRNA level including exon skipping. Base or sequence changes can for example be achieved by RNA-guided site-specific DNA cleavage, by cut and paste mechanisms exploiting trans-splicing, trans-splicing ribozymes, chimeraplasts, splicosome-mediated RNA trans-splicing, or by exploiting group II or retargeted introns, or by exploiting insertional mutagenesis mediated by viruses or exploiting targeted genomic insertion using prokaryotic, eukaryotic or viral integrase systems. As nucleic acids are the carriers of the building plans of living systems and as they participate in many cellular processes in a direct and indirect manner, in theory any cellular process can be influenced by the introduction of nucleic acids into cells from outside. Notably, this introduction can be carried out directly in vivo and ex vivo in cell or organ culture followed by transplantation of thus modified organs or cells into a recipient. Complexes of the present invention with nucleic acids as active agents may be useful for all purposes described above.

Composition

As disclosed above, the composition in accordance with the invention comprises a nucleic acid, in particular RNA, preferably single stranded RNA such as mRNA, and the copolymer in accordance with the invention.

The invention encompasses also a composition which consists of the nucleic acid, in particular RNA, preferably single-stranded RNA such as mRNA, and the copolymer in accordance with the invention. However, the composition may also comprise further components, e.g. components for lipid formulation and/or components that exert an effector function during delivery of the nucleic acid to and into a cell. Typically, the combined weights of the nucleic acid and the copolymer in accordance with the invention account for 50 wt % or more, preferably 70 wt % or more, of the total weight of the composition.

It will be understood that the compositions in accordance with the invention generally provide an association of the nucleic acid, in particular RNA, preferably single-stranded RNA such as mRNA, with the copolymer and optional further components, which are associated in a finite entity, stable enough to maintain association of a significant proportion of said components until reaching a biological target or the surroundings of a biological target during an application, for example during a desired route of nucleic acid, in particular RNA, preferably single-stranded RNA such as mRNA, delivery.

Due to the presence of the protonatable amino groups in the copolymer in accordance with the invention, this copolymer may comprise cationic charges in the repeating units of formula (a) and/or (b), such that the copolymer forms a cation, typically an oligo- or polycation containing a plurality of cationic moieties, in the presence of protons, e.g. in water or aqueous solutions, or in the presence of a proton donating acid. Thus, preferably, the composition in accordance with the invention contains or consists of a complex of nucleic acid, in particular RNA, preferably single-stranded RNA such as mRNA, and a copolymer in accordance with the invention which is a cationic copolymer. It will be understood that a cationic copolymer and an anionic nucleic acid are generally associated via electrostatic interaction in such a complex. However, other attractive interactions may also participate in stabilizing the complex, including hydrogen bonds and covalent bonds.

In the compositions of the present invention, the copolymer and nucleic acid, in particular RNA, preferably single-stranded RNA such as mRNA, are typically contained, e.g., in a ratio weight copolymer/weight nucleic acid (w/w) of 0.25/1-50/1, preferably of 0.5/1-30/1, more preferably of 1/1-20/1.

More preferably, in cases wherein the composition contains a complex of the nucleic acid, particularly RNA, preferably single-stranded RNA such as mRNA, and a cationic copolymer in accordance with the invention, relative ratios of the copolymer and the nucleic acid, in the compositions of the invention may be selected considering the degree of mutual charge neutralization. In nucleic acid, particularly RNA, preferably single-stranded RNA such as mRNA, delivery with complexes of the nucleic acid, with a cationic copolymer, in general, amounts of the cationic copolymer are mixed with a given quantity of the nucleic acid, which lead to at least a charge neutralization of the nucleic acid's negative charges, preferably to an overcompensation of the nucleic acid's negative charges.

Suitable ratios between cationic copolymer and nucleic acid, particularly RNA, preferably single-stranded RNA such as mRNA can easily be determined by gel retardation assays, fluorescence quenching methods such as the ethidium bromide displacement/quenching assay, by particle sizing and zeta potential measurements. Useful ratios between copolymer and nucleic acid, particularly RNA, preferably single-stranded RNA such as mRNA are usually characterized by at least partial, preferably complete retardation of the nucleic acid comprised in the complex with the cationic copolymer when subjected to electrophoresis in an agarose gel, by a high degree of fluorescence quenching of dyes such as ethidium bromide, RiboGreen or YOYO when intercalated in the nucleic acids or by the formation of (nano)particles upon mixing copolymer and nucleic acid.

For compositions containing the chemically well-defined cationic copolymers of the present invention, the calculated N/P ratio is a suitable factor to choose and define the relative ratios of the copolymer and the nucleic acid, particularly RNA, preferably single-stranded RNA such as mRNA. The N/P ratio designates the molar ratio of the protonatable nitrogen atoms in the repeating units (a) and (b) of the copolymer of the present invention over the phosphate groups of the nucleic acid in the composition of the present invention. The N/P ratio is an established parameter for the characterization of such complexes of nucleic acid with cationic vehicles. It will be understood by the skilled reader that the nitrogen atoms in the amino groups linking the repeating units (a) and (b) to neighboring repeating units and terminal amino groups are considered as protonatable nitrogen atoms. On the other hand, nitrogen atoms in amide bonds (which are not generally present in the copolymers of the invention), would not count as protonatable nitrogen atoms. For the compositions of the present invention containing a cationic copolymer of the invention and nucleic acid, particularly RNA, preferably single-stranded RNA such as mRNA, the N/P ratio can be conveniently calculated e.g. according to the formula $$\frac{N}{P} \frac{w_p \times n}{M_{wp}} + \frac{w_{na}}{M_{base}}$$

where $w_p$ is the weight of the copolymer in grams, n is the number of protonatable amino groups per repeating unit, $M_{wp}$ is the mean molecular weight of the repeating units (a) and (b) contained in the copolymer, $w_{na}$ is the weight of the nucleic acid in grams and $M_{base}$ is the average molecular weight of a nucleotide in the nucleic acid, e.g. 346 g/mol in the case of RNA.

Specifically for the copolymers of the present invention, n is 1. $M_{wp}$ can be calculated based on the ratio of the polymerized repeating units, e.g. determined via NMR, and their respective molecular weights. For example, in a branched copolymer containing polymerized units (a2) and (b2) with molecular weights of 42 g/mol (a2) and 56 g/mol (b2), respectively, in a molar ratio of (a)/(b) of 0.9/1.0, $M_{wp}$ calculates as $$Mwp = \frac{0.9 \times 42 + 1.0 \times 56}{(0.9 + 1.0)} = 49.4$$

In binary complexes of in accordance with the invention consisting of the copolymer in accordance with the invention and the nucleic acid, particularly RNA, preferably single-stranded RNA such as mRNA, for nucleic acid delivery in accordance with the invention, relative amounts of the copolymer to the nucleic acid should preferably be used which provide an N/P ratio resulting in a positive zeta potential of the final binary composition. In the context of the present invention, for binary compositions of the present invention, N/P ratios from 1 to 100 are preferred, more preferred are N/P ratios from 3 to 60, and most preferred are N/P ratios from 4 to 44.

The composition of the invention optionally comprises other components, in particular components that may exert an effector function during nucleic acid, in particular RNA, preferably single-stranded RNA such as mRNA, delivery to and into a cell. Such components can be but are not limited to polyanions, lipids, polycations other than the copolymers of the present invention including cationic peptides, shielding oligomer or polymers, poloxamers (also known as pluronics), poloxamines, targeting ligands, endosomolytic agents, cell penetrating and signal peptides, magnetic and non-magnetic nanoparticles, RNAse inhibitors, fluorescent dyes, radioisotopes or contrast agents for medical imaging. The term "effector function" encompasses any function that supports achieving an intended biological effect of a nucleic acid, in particular RNA, preferably single-stranded RNA such as mRNA, of the composition at or in a biological target or the surrounding of a biological target. For example, compositions for nucleic acid delivery have been formulated to comprise non-coding nucleic acids or non-nucleic acid polyanions as stuffer materials (Kichler et al. 2005, J Gene Med, 7, 1459-1467). Such stuffer materials are suitable for reducing the dose of a nucleic acid having an intended biological effect while maintaining the extent or degree of that effect obtained at a higher nucleic acid dose in the absence of such stuffer material. Non-nucleic acid polyanions have also been used to obtain prolonged in vivo gene expression at reduced toxicity (Uchida et al. 2011, J Control Release, 155, 296-302). The compositions of the present invention can also comprise cationic, anionic or neutral lipids such as is the case in lipopolyplexes (Li and Huang in "Nonviral Vectors for Gene Therapy", Academic Press 1999, Chapter 13, 295-303). Furthermore, compositions of the present invention can comprise oligo- or polycations other than the copolymers of the present invention. Such additional oligo- or polycations can be useful to achieve a desired degree of compaction of a nucleic acid or in the case of polycationic peptides can have a nuclear localization signal function such as described previously (Ritter et al. 2003, J Mol Med, 81, 708-717). Shielding polymers such as poly(ethylene glycol) (PEG) can as well be comprised in the compositions of the present invention and are used frequently to stabilize polyplexes and lipoplexes against aggregation and/or undesired interactions in a biological environment (opsonization), for example interactions with serum components, blood cells or extracellular matrix. Shielding can also be suitable to reduce the toxicity of nucleic acid-comprising compositions (Finsinger et al. 2000, Gene Ther, 7, 1183-1192). Shielding polymers such as PEG can be covalently coupled directly to copolymers of the present invention. The coupling can be achieved, e.g. to terminal groups (c), or to an amino group of the repeating units of formulae (a1), (b1) or (b3).

Polyvinyl derivatives such as PVP and poloxamers have been found useful to enhance transfection upon intramuscular injection (Mumper et al. 1996, Pharm Res, 13, 701-709, Lemieux et al. 2000, Gene Ther, 7, 986-991) and hence can be useful to be comprised in the compositions of the present invention.

Targeting ligands including antibodies comprised in compositions for nucleic acid delivery are useful for preferential and improved transfection of target cells (Philipp and Wagner in "Gene and Cell Therapy—Therapeutic Mechanisms and Strategy", 3rd Edition, Chapter 15. CRC Press, Taylor & Francis Group LLC, Boca Raton 2009). A targeting ligand can be any compound that confers to compositions of the present invention a target recognition and/or target binding function in a direct or indirect manner. In most general terms, a target is a distinct biological structure to which a targeting ligand can bind specifically via molecular interaction and where such binding will ultimately lead to preferential accumulation of the nucleic acid comprised in the composition in a target tissue and/or at or in a target cell. Similarly to PEG chains, targeting ligands can be coupled e.g. to terminal groups (c), or to an amino group of the repeating units of formulae (a1), (b1) or (b3).

Furthermore, endosomolytic agents such as endosomolytic peptides (Plank et al. 1998, Adv Drug Deliv Rev, 34, 21-35) or any other compound that is suited to enhance the endosomal release of an endocytosed nucleic acid are useful components of compositions of present inventions. Similarly, cell penetrating peptides (in another context also known as protein transduction domains) (Lindgren et al. 2000, Trends Pharmacol Sci, 21, 99-103) can be useful components of the composition of the present invention in order to mediate intracellular delivery of a nucleic acid. The so-called TAT peptide falls within this class and also has nuclear localization function (Rudolph et al. 2003, J Biol Chem, 278, 11411-11418).

Magnetic nanoparticles which may be comprised in compositions of the present invention are useful for physical targeting of delivery by magnetic force and for a drastic enhancement of the efficiency of nucleic acid transfer, a mechanism also known as Magnetofection (EP1297169; Plank et al. 2011, Adv Drug Deliv Rev, 63, 1300-1331). Similarly, a composition of the present invention can also be a non-magnetic or magnetic microbubble used for physical enhancement and targeting of nucleic acid delivery via ultrasound and optionally magnetic field application (Holzbach et al. 2010, J Cell Mol Med, 14, 587-599, Vlaskou et al. 2010, Adv Funct Mater, 20, 3881-3894). Quantum dots (Zintchenko et al. 2009, Mol Ther, 17, 1849-1856), radioactive tracers and contrast agents for medical imaging can be used advantageously for tracking nucleic acid delivery and to determine the biodistribution of compositions for nucleic acid delivery. Summarizing, numerous effectors for nucleic acid delivery have been described and can be useful components in compositions comprising nucleic acid, in particular RNA, preferably single-stranded RNA such as mRNA and a copolymer in accordance with the invention.

It is well known to those skilled in the art that there is a large degree of flexibility with respect to the amount of substance of each component comprised in the composition according to the present invention. For example, so-called monomolecular binary polyplexes have been described for plasmid DNA where the composition consists of nanoparticles formed upon mixing of the polycation and the plasmid DNA which comprise exactly a single plasmid DNA molecule and as many polycation molecules which are required for charge neutralization or charge overcompensation (positive over negative) (DeRouchey et al. 2006, J Phys Chem B. 110(10):4548-54). For PEI-DNA, complexes at N/P ratios which are often used in transfections, it was found by fluorescence correlation spectroscopy that they contain on average 3.5 (+/−1) DNA plasmid molecules and 30 PEI molecules while about 86% of the PEI molecules used for preparing the complexes were in a free form (Clamme et al. 2003, Biophys J 84,1960-1968). In the other extreme, it was found that aggregated complexes of PEI and plasmid DNA, putatively comprising a large number (tens to hundreds) of the component molecules performed better in transfection than small discrete PEI-DNA nanoparticles (Ogris et al. 1998, Gene Ther, 5, 1425-1433; Ogris et al. 2001, AAPS PharmSci, 3, E21). Hence, the composition according to the present invention can be a particle, in particular a nanoparticle comprising a few nucleic acid, in particular RNA, preferably single-stranded RNA such as mRNA, molecules but may as well be a macroscopic object such as a precipitate or a dry powder comprising enormous numbers of nucleic acid, in particular RNA, preferably single-stranded RNA such as mRNA, molecules. Summarizing, the compositions of the current invention are characterized by the input ratios of their components before self-assembly. Typical input w/w ratios of individual components relative to the nucleic acid, in particular RNA, preferably single-stranded RNA such as mRNA, component are between 1 and 50. The N/P ratio is a suitable measure of the input ratio for binary compositions containing the copolymer of the invention and the nucleic acid, in particular RNA, preferably single-stranded RNA such as mRNA when the copolymer is chemically well defined. As noted above, values for the N/P ratio of 1 to 100 are preferred, more preferred are N/P ratios from 3 to 60, and most preferred are N/P ratios from 4 to 44.

If the composition of the present invention comprises further components, an assignment of an N/P ratio may be ambiguous. In this case, suitable input ratios are determined by experiment including but not limited to gel retardation assays, fluorescence quenching assays such as the ethidium bromide displacement/quenching assay, by particle sizing and zeta potential measurements and by functional assays such as transfection assays as described herein. In ternary complexes comprising an additional polyanion or shielding polymers, the net charge ratio (positive over negative) may be smaller than 1 and the zeta potential may be neutral or negative.

The composition of the invention can be produced as described below. Typically, the nucleic acid, in particular RNA, preferably single-stranded RNA such as mRNA with a negative charge and the copolymers of the present invention preferably in a cationic form can self-assemble when brought in contact especially in a suitable solvent. After the self-assembly process, the composition of the present invention may be separated from any un-incorporated components and in the same step the suspension medium can be replaced by centrifugation or by ultrafiltration or size exclusion chromatography or dialysis or any related methods. The stoichiometry of the components of the composition of the present invention, purified or un-purified, can be determined by a variety of analytical methods including spectroscopic methods such as UV/VIS spectrometry or fluorescence correlation spectroscopy (DeRouchey et al. 2006, J Phys Chem B. 110(10):4548-54), by orthogonal fluorescence or radioisotope labelling of the individual components, by NMR and IR spectroscopy or chromatographic analysis and quantitation upon disassembly of the composition. Disassembly can be achieved for example by the addition of excess polyanion such as heparin as described herein or chondroitin sulphate or by the addition of sodium dodecylsulphate.

The present invention also relates to a method for producing the composition of the invention. Copolymers in accordance with the present invention can be produced and purified as described herein. The copolymers can be stored in aqueous solution or in dried form, such as a dried powder, in which case they can be redissolved in aqueous medium, preferably water, before producing the composition. The pH of the solution is adjusted to neutral or slightly acidic (down to pH 4.5) with an acid, preferably with hydrochloric or citric acid, if required. In the case of RNA, preferably single-stranded RNA such as mRNA, being the nucleic acid comprised in the composition it is preferred that the pH is adjusted to about 4.5 to 5.5, preferably to about 4.9 to 5.1, more preferably to about 5.0. Nucleic acids are produced and purified according to the state of the art well known to the one skilled in the art. The nucleic acid is provided as solution in aqueous medium, preferably water. Optionally, either the copolymer or the RNA as nucleic acid or both are chemically linked with effector molecules such as targeting ligands, signal peptides, cell penetrating peptides, endosomolytic substances or shielding polymers. However, depending on the chemical nature of the effector molecules, they may not need to be attached by chemical bond but can rather be incorporated in the composition of the present invention by self-assembly based on non-covalent binding, i.e. electrostatic, hydrophobic or Van-der-Waals interaction with any of the other components of the composition. For this purpose, it may be advantageous to adjust the ionic strength, type of counterion, pH or organic solvent content of individual component solutions.

As an alternative to the mixing procedure described above, the nucleic acid, in particular RNA, preferably single-stranded RNA such as mRNA, and copolymer component can be mixed with an automated device for micromixing such as described for example by Hirota et al. (Hirota et al. 1999, Biotechniques, 27, 286-290) or Kasper et al. (Kasper et al. 2011, Eur J Pharm Biopharm, 77, 182-185) or by microfluidic focussing such as reviewed by Xuan et al. (Xuan et al. 2010, Microfluidics and Nanofluidics, 9, 1-16).

The composition of the present invention comprising nucleic acid, in particular RNA, preferably single-stranded RNA such as mRNA, can then be prepared by self-assembly upon mixing the solutions of the components. Self-assembly can be accomplished by hand mixing using pipetting and shaking/vortexing or using an automated device for micromixing such as described for example by Hirota et al. (Hirota et al. 1999, Biotechniques, 27, 286-290) or Kasper et al. (Kasper et al. 2011, Eur J Pharm Biopharm, 77, 182-185) or by microfluidic focussing such as reviewed by Xuan et al. (Xuan et al. 2010, Microfluidics and Nanofluidics, 9, 1-16). If the composition of the present invention comprises further components in addition to the nucleic acid, in particular RNA, preferably single-stranded RNA such as mRNA, and the copolymer of the present invention, sequential mixing can be required. In this case, any further component may be added after self-assembly of the copolymer and the nucleic acid, or it may be added to either of these before mixing. The most suitable sequence of mixing steps will be dependent on the chemical nature of additional components. For example, if the additional component is negatively charged, it may be most suitable to add it to the nucleic acid component before mixing with the copolymer or to a pre-formed complex of the copolymer and the nucleic acid, where the copolymer of the present invention is present in excess in terms of the ratio of positive charges over the sum of the negative charges of the nucleic acid and the anionic additional component. Vice-versa, if the additional component is cationic it may be most suitable to add it to the copolymer of the invention before mixing with the nucleic acid. Or it may be used at a stoichiometry to partially neutralize the negative charges of the nucleic acid followed by mixing with the solution of the copolymer of the present invention. In the case of nucleic acid, in particular RNA, preferably single-stranded RNA such as mRNA comprising complexes for magnetofection, it has been shown that salt-induced colloid aggregation is a suitable means for preparing compositions comprising a nucleic acid, a polycation or a cationic lipid and magnetic particles (EP1297169). In the special case of the nucleic acid, in particular RNA, preferably single-stranded RNA such as mRNA, component being a cationic oligonucleotide, a polyanion can be used to self-assemble the copolymer of the present invention with the nucleic acid. In this case, the copolymer of the present invention is mixed with the cationic oligonucleotide followed by mixing with the polyanion. It will be readily apparent to the one skilled in the art that numerous formulation options are available to obtain the composition of the present invention. The concentrations of the individual components are chosen according to the intended use of the composition of the present invention. Relevant parameters are the final concentration of the nucleic acid, in particular RNA, preferably single-stranded RNA such as mRNA component and the ratio of components as described above. For nucleic acid, in particular RNA, preferably single-stranded RNA such as mRNA delivery in cell culture, final nucleic acid concentrations between 1 and 100 µg/ml are generally preferred. For in vivo applications, useful exemplary final nucleic acid concentrations can be up to 5 mg/ml.

The composition of the present invention can be stored in aqueous suspension or can be dried. Hence, in one preferred embodiment, the composition of the present invention is stored in dried form, optionally freeze-dried (lyophilized) form. In a more preferred embodiment, the dried or lyophilized complex or composition also comprises a lyoprotectant. Lyoprotectants are molecules which protect (freeze-) dried material. Such molecules are typically polyhydroxy compounds such as sugars (mono-, di- and polysaccharides), polyalcohols and their derivatives. Trehalose and sucrose are known to be natural protectants for drying processes. Trehalose is produced by a variety of plants, fungi and invertebrate animals that remain in a state of suspended animation during periods of drought (also known as anhydrobiosis). Sugars such as trehalose, lactose, raffinose, sucrose, mannose, sorbitol, mannitol, xylitol, polyethylenglycol, dextrins, urea, maltodextrins, fructans, maltooligosaccharides, manno-oligosaccharides, cycloinulohexaose, hydroxyethyl starch, dextrans, inulin, polyvinylpyrrolidone or amino acids such as tryptophan, glycin and phenylalanine are particularly suitable lyoprotectants in the scope of the present invention. Most preferably trehalose is used in this context.

Pharmaceutical Aspects

In a further aspect, the present invention relates to the use of the composition of the present invention or of the copolymer of the present invention for delivering a nucleic acid, in particular RNA, preferably single-stranded RNA such as mRNA, to tissue or into a target cell. The term "delivering a nucleic acid, in particular RNA, preferably single-stranded RNA such as mRNA, to a cell" preferably means transfer of the nucleic acid, in particular RNA, preferably single-stranded RNA such as mRNA, into the cell. Said use can be in vivo or in vitro.

The present invention also relates to a method for delivering a nucleic acid, in particular RNA, preferably single-stranded RNA such as mRNA, to a target cell or tissue comprising the step of bringing a composition according to the invention into contact with the target cell or tissue. Such a method can be carried out in vitro or in vivo. The bringing into contact may be achieved by means and methods known to the person skilled in the art. For example, if the method is carried out in vitro, the bringing into contact can be achieved by cultivating the cells in the presence of the composition in the culture medium or by adding the composition to the cells. If the method is carried out in vivo, the bringing into contact with cells or tissues can, e.g., be achieved by the administration of the composition to an individual by routes of administration known to the person skilled in the art, in particular by any route of administration that is usually employed in the field of genetic therapy. Possible ways of formulating the composition and of administering it to an individual are also described further below.

The term "in vivo" refers to any application which is effected to the body of a living organism wherein said organism is preferably multicellular, more preferably a mammal and most preferably a human. The term "in vitro" refers to any application which is effected to parts of the body of a living organism isolated and outside said organism, e.g. cells, tissues and organs, wherein said organism is preferably multicellular, more preferably a mammal and most preferably a human.

The present invention also relates to a pharmaceutical composition comprising the composition in accordance with the invention and optionally a pharmaceutically acceptable carrier and/or diluent. In this context, it will be understood that the composition in accordance with the invention as defined herein may be/may be used as a pharmaceutical composition on its own. The term "pharmaceutical composition" refers to a pharmaceutically acceptable form of the composition of the present invention which can be administered to a subject. The pharmaceutical composition is suitable for use in the treatment of the human or animal body by therapy (including prophylaxis).

The term "pharmaceutically acceptable form" means that the composition is formulated as a pharmaceutical composition, wherein said pharmaceutical composition may further comprise a pharmaceutically acceptable carrier and/or diluent. Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. The dosage regimen will be determined by the attending physician and clinical factors. As is well known in the medical arts, dosages for any one subject depend upon many factors, including the subject's size, body surface area, age, the particular compound to be administered, sex, time and route of administration, general health, and other drugs being administered concurrently. A typical dose of active substances can be, for example, in the range of 1 ng to several grams. Applied to nucleic acid, in particular RNA, preferably single-stranded RNA such as mRNA, therapy, the dosage of the nucleic acid for expression or for inhibition of expression should correspond to this range; however, doses below or above this exemplary range are envisioned, especially considering the aforementioned factors. Generally, the regimen as a regular administration of the pharmaceutical composition should be in the range of 0.1 µg to 10 mg units per kilogram of body weight per day. If the regimen is a continuous infusion, it should also be in the range of 1 µg to 10 mg units per kilogram of body weight, respectively. Progress can be monitored by periodic assessment. Dosages will vary but a preferred dosage for intravenous administration of nucleic acid, in particular RNA, preferably single-stranded RNA such as mRNA, as constituents of the composition of the present invention is from approximately $10^6$ to $10^{19}$ copies of the nucleic acid molecule.

The term "administered" encompasses any method suitable for introducing the composition into the body of a subject. Administration of suitable compositions may be effected in different ways, e.g., by intravenous, intraarterial, intraperitoneal, subcutaneous, transdermal, intrathecal, intramuscular, topical, intradermal, intranasal, pulmonary by inhalation or intrabronchial or oral or rectal administration. The compositions of the present invention may in particular be administered as a gene-activated matrix such as described by Shea et al. (Shea et al. 1999, Nat Biotechnol, 17, 551-554) and in EP1198489.

In principle, the pharmaceutical compositions of the invention may be administered locally or systemically. Administration will preferably be parenterally, e.g., intravenously, although other ways of administration are within the scope of the invention. Administration directly to the target site, e.g., by catheter to a site in a blood vessel, is also conceivable. Administration can, for example, also occur by direct injection into a target site such as a tumor. Also within the scope of the invention is administration by aerosolization or nebulization or oral administration. Preparations for parenteral administration include sterile aqueous or non-aqueous solutions, suspensions, and emulsions. Examples of non-aqueous solvents are propylene glycol, polyethylene glycol, fluorocarbons, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition may comprise further agents such as interleukins or interferons depending on the intended use of the pharmaceutical composition.

In another embodiment the present invention relates to a method of treatment comprising administering the pharmaceutical composition of the present invention to a patient in order to have the nucleic acid, in particular RNA, preferably single-stranded RNA such as mRNA, contained in said composition cause a preventive or therapeutic effect. Notably, the term "patient" comprises animals and humans.

By administering the pharmaceutical composition of the present invention, diseases can be treated or prevented. The term "disease" refers to any conceivable pathological condition that can be treated, prevented or vacined against by employing an embodiment of the present invention. In a preferred embodiment of said method, said diseases may be inherited, acquired, infectious or non-infectious, age-related, cardiovascular, metabolic, intestinal, neoplastic (in particular cancer) or genetic. A disease can be based, for example, on irregularities of physiological processes, molecular processes, biochemical reactions within an organism that in turn can be based, for instance, on the genetic equipment of an organism, on behavioural, social or environmental factors such as the exposure to chemicals or radiation. In a particularly preferred embodiment, the pharmaceutical composition of the present invention is used for treatments as disclosed in the patent application WO2011/012316.

In line with the above-described method of treatment, the present invention refers in another embodiment to the use of the composition of the present invention for the preparation of a pharmaceutical composition for the treatment of a disease that can be treated by providing said nucleic acid, in particular RNA, preferably single-stranded RNA such as mRNA, contained in said composition to a tissue or organ within the body of a patient affected by a disease.

For further illustration, preferred aspects of the invention are summarized in the following aspects, which form part of the preceding general disclosure and the preferred embodiments disclosed therein applies as well.

1. A statistical copolymer comprising a plurality of repeating units (a) independently selected from repeating units of the following formulae (a1) and (a2):

and
a plurality of repeating units (b) independently selected from repeating units of the following formulae (b1) to (b4):

wherein the molar ratio of the sum of the repeating units (a) to the sum of the repeating units (b) lies within the range of 0.7/1.0 to 1.0/0.7, and
wherein one or more of the nitrogen atoms of the repeating units (a) and/or (b) contained in the copolymer may be protonated to provide a cationic copolymer.

2. The copolymer of aspect 1, which is a branched or dendritic copolymer comprising one or more types of repeating units selected from repeating units (a2), (b2) and (b4).

3. The copolymer of aspect 1, which is a linear copolymer comprising repeating units (a1) and (b1).

4. The copolymer of any of aspects 1 to 3, wherein the repeating units (a) and (b) account for 80 mol % or more of all repeating units in the copolymer.

5. The copolymer of any of aspects 1 to 3, wherein all of the repeating units in the copolymer are repeating units (a) or (b).

6. The copolymer of any of aspects 1 to 3, wherein repeating units (a) selected from (a1) and (a2) and repeating units (b) selected from (b1) and (b2) account for 80 mol % or more of all repeating units in the copolymer.

7. The copolymer of any of aspects 1 to 3, wherein all of the repeating units in the copolymer are repeating units (a) selected from (a1) and (a2) or repeating units (b) selected from (b1) and (b2).

8. The copolymer of any of aspects 1 to 7, which is a random copolymer.

9. The copolymer of any of aspects 1 to 8, wherein the total number of repeating units (a) and repeating units (b) is 20 or more, preferably 50 or more and more preferably 100 or more.

10. The copolymer of any of aspects 1 to 9, wherein the total number of repeating units (a) and repeating units (b) is 5,000 or less, preferably 2,500 or less, and more preferably 1,000 or less.

11. The copolymer of any of aspects 1 to 10, which has a weight average molecular weight ranging from 2,000 to 250,000 Da, preferably from 5,000 to 50,000 Da.

12. The copolymer of any of aspects 1 to 11, wherein the terminal groups of the copolymer comprise one or more types of groups (c) independently selected from groups of the formulae (c1) to (c3):

(c1)

(c2)

(c3).

13. The copolymer of aspect 12, wherein the terminal groups of the copolymer comprise one or more types of groups (c) independently selected from groups of the formulae (c1) and (c2).

14. The copolymer of any of aspects 1 to 13, wherein the molar ratio of the repeating units (a) to the repeating units (b) lies within the range of 0.8/1.0 to 1.0/0.8.

15. The copolymer of any of aspects 1 to 14, which is a cationic copolymer.

16. The copolymer of any of aspects 1 to 15, which is obtainable by polymerizing a monomer mixture comprising aziridine, azetidine, and optionally pyrrolidine.

17. A composition comprising a nucleic acid and a copolymer in accordance with any of aspects 1 to 16.

18. The composition of aspect 17, wherein the nucleic acid is an RNA.

19. The composition of aspect 17, wherein the nucleic acid is a single stranded RNA.

20. The composition of aspect 17, wherein the nucleic acid is mRNA, preferably modified mRNA.

21. The composition of any of aspects 17 to 20, wherein the copolymer is a cationic copolymer, and wherein the cationic copolymer forms a complex with the nucleic acid.

22. The composition of any of aspects 1 to 21, which is in lyophilized form.

23. The composition of aspect 22, which further comprises a lyoprotectant.

24. The composition of aspect 23, wherein the lyoprotectant is trehalose.
25. The composition of any of aspects 1 to 22, which is a pharmaceutical composition.
26. A pharmaceutical composition comprising a composition of any one of aspects 17 to 25, and optionally an additional pharmaceutically acceptable carrier and/or diluent.
27. Use of a copolymer of any of aspects 1 to 16 for delivering a nucleic acid into a cell.
28. Use of a composition or a pharmaceutical composition of any of aspects 17 to 26 for delivering a nucleic acid into a cell.
29. The use of aspect 27 or 28, wherein the nucleic acid is an RNA.
30. The use of aspect 27 or 28, wherein the nucleic acid is a single stranded RNA.
31. The use of aspect 27 or 28, wherein the nucleic acid is mRNA, preferably modified mRNA.
32. A method for delivering a nucleic acid to a target cell or tissue comprising the step of bringing a composition or pharmaceutical composition of any one of aspects 17 to 26 into contact with the target cell or tissue.
33. A method for the production of the copolymer of any one of aspects 1 to 15, comprising the step of polymerizing a monomer mixture comprising aziridine, azetidine, and optionally pyrrolidine.

EXAMPLES

Example 1

Materials:
Production of Chemically Modified Luc mRNA
To generate template for the in-vitro-transcription (IVT) the plasmid pVAXA120-Luc was linearized by restriction digestion with NotI. Template was further purified by Chloroform-Ethanol-Precipitation. Quality of template was determined by native agarosegel electrophoresis. IVT was carried out with a standard IVT mix containing ribonucleotide triphosphates and T7 RNA Polymerase. Modifications were introduced using 25% of 5-methyl-cytidine-5'-triphosphate and 25% of 2-thio-uridine-5'-triphosphate. Capping was performed using the Vaccinia virus Capping Enzyme, rGTP and S-Adenosyl methionine (SAM) as a methyl donor to add a 7-methylguanylate cap-0 structure (m7GpppG) to the 5'end of the mRNA. Purification of mRNA was performed by ammonium acetate precipitation. Modified Luc RNA was resuspended in aqua ad injectabilia and quality control was performed using UV-measurement, native agarose gel electrophoresis and transfection in NIH3T3 cells.

Polymers and Mean Molecular Weights of Polymer Repeating Unit:
The polymers were synthesized from aziridine (E), azetidine (P) or a stoichiometric mixture of aziridine (E) and azetidine (P) at molar ratios of monomers (E:P) of 1:0, 0.8:1 and 0:1. Aziridine and Azetidine were homopolymerized and copolymerized starting from a solution of the monomers in water (total concentration of monomer(s): 50% w/w). Polymerizations were conducted at 130° C. for 20-70 h with 0.001 equivalent sulphuric acid. The homopolymers with a E:P ratio of 1:0 and 0:1, respectively, were produced for comparative purposes.
In this manner, random branched copolymers of ethylamine (—$CH_2$—$CH_2$—N<; "E"; molecular weight 42 g/mol) and propylamine (—$CH_2$—$CH_2$—$CH_2$—N<; "P"; molecular weight 56 g/mol) repeating units reflecting the stoichiometry of the monomers were prepared. The mean molecular weight of the polymerized units was calculated according to the formula $$Mw = \frac{E \times 42 + P \times 56}{(E + P)}$$

This yields the following results:

| E | P | Mean Mw |
|---|---|---------|
| 1 | 0 | 42.00 |
| 0.8 | 1 | 49.78 |
| 0 | 1 | 56.00 |

Stock Solutions:
Polymer stock solution: 0.5 mg/ml in aqua ad injectabilia
mRNA stock solution: 0.05 mg/ml stock solution in aqua ad injectabilia N/P Ratio and Preparation of mRNA Complexes with Polymers
The N/P ratio reflects the input molar ratio of nitrogen in a given quantity of polymer to phosphate in a given quantity mRNA used to prepare a polymer-mRNA complex. The mean molecular weight of a ribonucleotide monophosphate in a mRNA is 346 g/mol. Hence, the volume of polymer stock solution ($v_{polymer}$) a given concentration ($c_{polymer}$) required for a given weight of mRNA ($w_{RNA}$) at a desired N/P ratio is as follows:

$$v_{polymer} = \frac{w_{RNA} \times Mw_{polymer} \times N/P}{346 \times c_{polymer}}$$

Accordingly, the volumes of polymer stock solutions given in the table below were diluted with the given volumes of aqua ad injectabilia to 25 µL in individual wells of row A and E, respectively, of a 96-well plate.

| N/P | 4 | 8 | 10 | 12 | 16 | 20 |
|-----|---|---|----|----|----|----|
| E:P = 1:0 (µL) | 1.21 | 2.43 | 3.03 | 3.64 | 4.86 | 6.07 |
| H2O (µL) | 23.79 | 22.57 | 21.97 | 21.36 | 20.14 | 18.93 |
| E:P = 0.8:1 (µL) | 1.44 | 2.88 | 3.60 | 4.32 | 5.75 | 7.19 |
| H2O (µL) | 23.56 | 22.12 | 21.40 | 20.68 | 19.25 | 17.81 |
| E:P = 0:1 (µL) | 1.62 | 3.24 | 4.05 | 4.86 | 6.47 | 8.09 |
| H2O (µL) | 23.38 | 21.76 | 20.95 | 20.14 | 18.53 | 16.91 |

Subsequently, 25 µL of mRNA stock solution (corresponding to 1.25 µg mRNA) were added to the polymer solutions to yield the desired N/P ratio. The wells in rows B to D and F to H, respectively, were provided with 25 µL aqua ad injectabilia each. After 30 min incubation, 25 µL of the complexes in row A or E, respectively, were transferred to row B or F, respectively using a multichannel pipettor and mixed. Subsequently, 25 µL were transferred from row B to row C or from F to G, respectively, mixed and from C to D or G to H, respectively.

Cells, Transfection and Luciferase Assay
HEK293 cell s(DSMZ ACC305,Lot21) were cultivated in DMEM,MEM,MEM each incl 10% FBS+1% P/S. Twenty-four hours prior transfection, the cells were seeded at a density of 5,000 cells in 100 µL cell culture medium in a 96-well plate.

Twenty μL each of the polymer-mRNA complex dilution series were transferred to the cells, corresponding to 125/62.5 ng mRNA per well. After 24 h of incubation, the cell culture supernatants were removed, the cells were washed with PBS and then provided with 100 μL of lysis buffer (25 mM Tris HCl, 0.1% TritonX 100, pH 7.8).

Luciferase assay: 80 μL of the lysate was filled into a well of a white 96-well plate and used for luciferase activity measurement in a Wallac Victor$^2$ (Perkin Elmer). For this purpose 100 μL of luciferase assay reagent (0.5 mM D-luciferin, 0.3 mM Coenzyme A, 33 mM DTT, 0.5 mM ATP, 1 mM magnesium carbonate, 2.7 mM magnesium sulfate, 0.1 mM EDTA, 20 mM tricine) was added and the chemiluminescence determined. Experiments were performed in triplicate.

Figure 1:
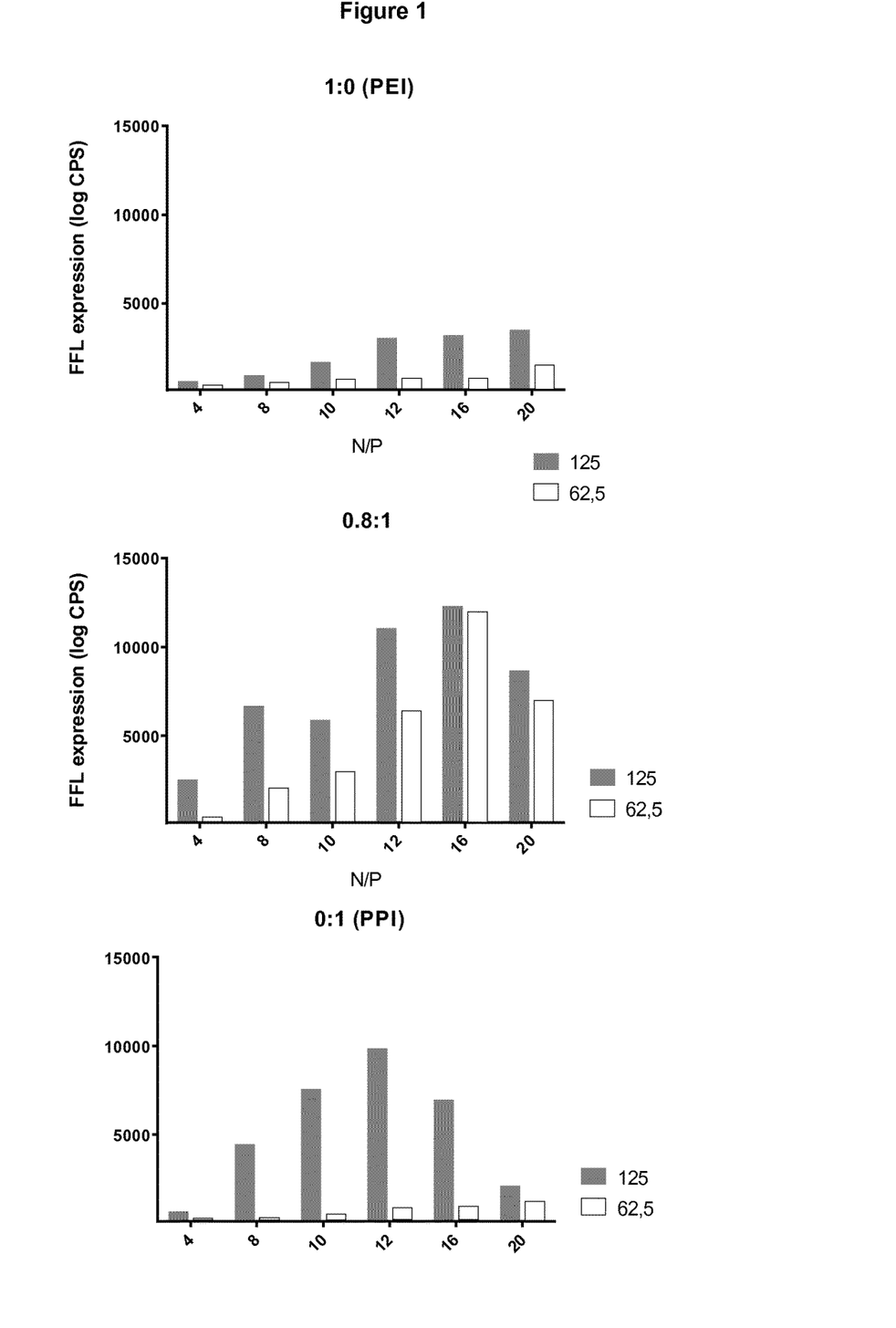

Results:

The experiment shows that chemically modified Luc mRNA complexed with copolymer (0.8/1) is more efficiently expressed after transfection of cells than either complexed with branched PEI (1/0) or PPI (0/1) (FIG. 1). Together this shows that the object of the present invention can be properly addressed by the method and pharmaceutical preparations according to the present invention.

Example 2

In Vivo Aerosol Application of Chemically Modified mRNA Encoding Firefly Luciferase (Luc) Formulated with Copolymers to the Lungs of Pig Chemicals
See example 1 above
Production of Chemically Modified Luc mRNA
See example 1 above
Experimental Procedure Sedation of the pig was initiated by premedication with azaperone 2 mg/kg body weight, ketamine 15 mg/kg body weight, atropine 0.1 mg/kg body weight and followed by insertion of an intravenous line to the lateral auricular vein. The pig was anesthetized by intravenous injection of propofol 3-5 mg/kg body weight as required. Anesthesia was maintained with continuous intravenous infusion of 1% propofol as required. Ventilation parameters were matched with endexpiratory carbon dioxide and adjusted if necessary. Anesthesia, respiratory and cardiovascular parameters were monitored continuously using pulse oximetry, capnography, rectal temperature probe and reflex status. The pig received infusion of balanced electrolyte solution at 10 ml/kg/h. Duration of the anesthesia was approximately 80-120 min. The pig was killed with bolus injection of pentobarbital 100 mg/kg of body weight via the lateral ear vein after sedation after aerosol application was completed (Aeroneb mesh nebulizer). Lungs were excised and sliced approximately 1 cm thick tissue specimens were collected from various lung regions followed by incubation in cell culture medium for 24 hrs at 37° C. (5% carbon dioxide) in an incubator. For measurement of luciferase activity tissue specimens were incubated in a medium bath comprising D-Luciferin substrate in PBS (100 μg/ml) at 37° C. for 30 min and subjected to ex vivo luciferase bioluminescent imaging (IVIS 100, Xenogen, Alameda, USA).

Preparation of Copolymer-mRNA Polyplexes

Polyplexes were formed using a two channel syringe pump (KDS-210-CE, KD Scientific). mRNA and copolymer (0.8/1, 1/0, 0/1 or PEI 25 kDa) were diluted each in 12.0 ml of double distilled water resulting in a concentration of 500 μg/ml mRNA (concentration of copolymer or branched PEI 25 kDa corresponding to an N/P ratio of 10). Both solutions were filled into a separate 20 mL syringe using the withdrawal function of the syringe pump at a speed of 5 mL/min. To mix both samples the two syringes were connected via a tubing (Safeflow Extension Set, B.Braun) was to a t-piece. Mixing was performed using the infusion function of the syringe pump at a speed of 40 mL/min. The complexes were incubated for 30 min at ambient temperature before use. It was observed within the course of the present invention that it is specifically advantageous to use only water without any buffers for complexation because otherwise nanoparticles may aggregate or be ineffective in mouse lungs (Rudolph et al., J. Mol Ther. 2005, 12: 493-501).

Figure 2:
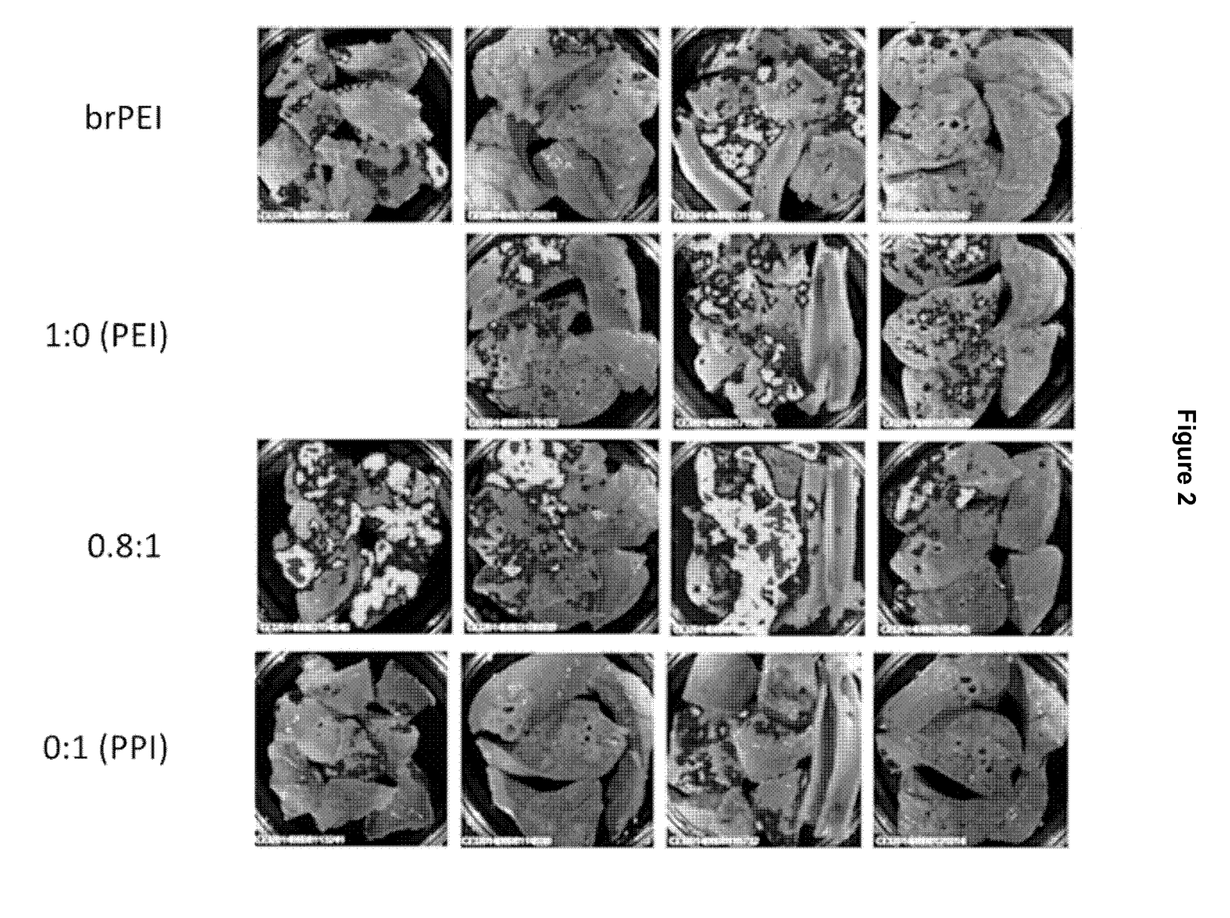

Results:

The experiment shows that chemically modified Luc mRNA complexed with copolymer (0.8/1) is more efficiently expressed in the lung cells of a pig upon pulmonary aerosol delivery than either complexed with PEI 25 kDa (1/0) or PPI (0/1) (FIG. 2). Together this shows that the object of the present invention can be properly addressed by the method and pharmaceutical preparations according to the present invention.

Example 3

Figure 3:
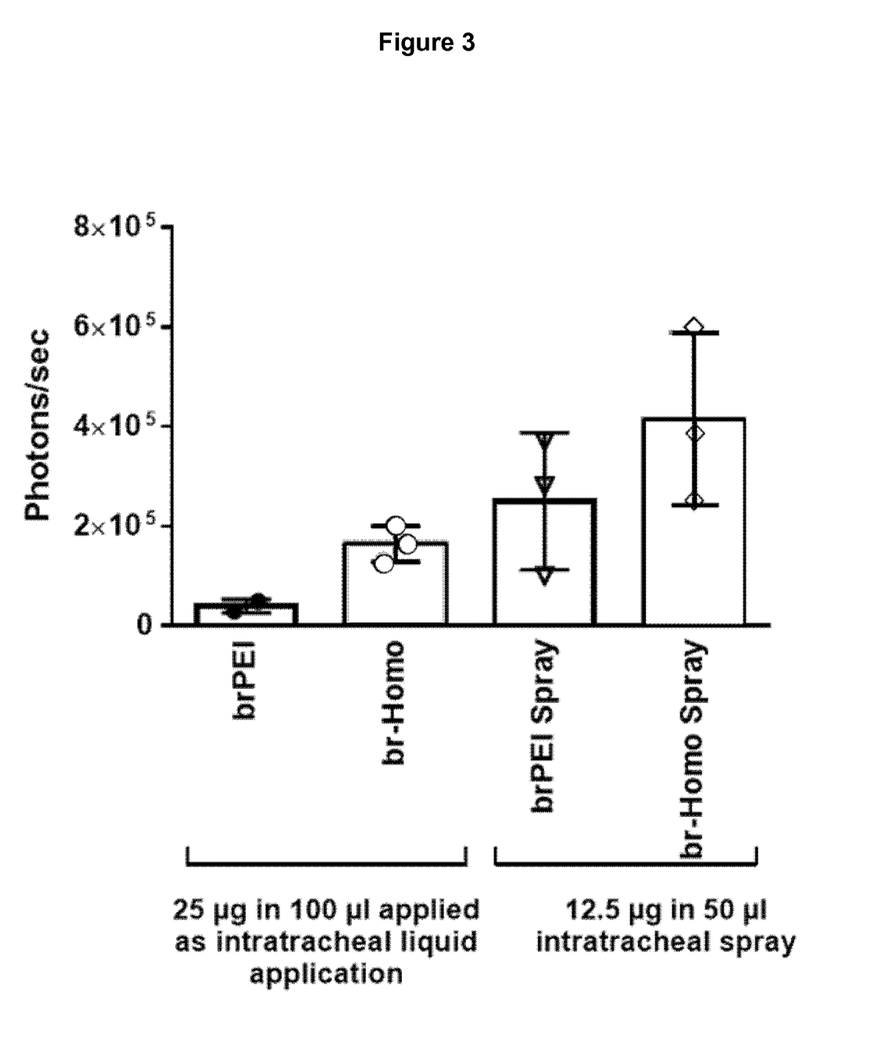

In Vivo Application of Chemically Modified mRNA Encoding Firefly Luciferase (Luc) Formulated with Copolymers to the Lungs of Mice Chemicals
See example 1 above
Production of Chemically Modified Luc mRNA
See example 1 above
Experimental Procedure Polyplexes of a branched 0.8/1 (ethylamine/propylamine units) copolymer ("br-Homo") and mRNA coding for firefly luciferase, and of branched polyethyleneimine ("br-PEI") and the mRNA were prepared and applied either as an intratracheal liquid (n=3), (25 μg of mRNA in a volume of 100 μL) or as an intratracheal spray (12.5 μg of mRNA in a volume of 50 μL) using a high-pressure Microsprayer device (PennCentury, USA). All experiments were approved by the local authorities (Regierung von Oberbayern) and were conducted according to the German Animal Welfare law. Female adult Balb/c mice were anesthetized in an Isoflurane inhalation chamber. Subsequently, the test formulations were applied directly into the trachea using a customized light source and a small animal spatula. Animals recovered from anesthesia within minutes. After 6 hours animals were anesthetized through intraperitoneal injection of Fentanyl/Midazolam/Medetomidin (0.05/5.0/0.5 mg/kg BW). D-Luciferin (1.5 mg diluted in 50 μL PBS) was applied on the nostrils of the anesthetized animals and thus inhaled into the deeper airways. Bioluminescence imaging was conducted using an IVIS Lumina XR Imaging System (Perkin Elmer, USA). Results are shown in FIG. 3.

DESCRIPTION OF FIGURES

FIG. 1

Polyplexes were formed using 0.8/1, 1/0 or 0/1 (ethylamine/propylamine units) copolymer and mRNA coding for firefly luciferase at indicated N/P ratios. After 24 h, HEK293 cells transfected with different amounts of mRNA (125 or 62.5 ng) were lysed and analyzed for luciferase activity.

FIG. 2

Polyplexes were formed using 0.8/1, 1/0 or 0/1 (ethylamine/propylamine units) copolymer, PEI (and commercially available branched PEI, 25 kDa, Sigma-Aldrich) and mRNA coding for firefly luciferase at N/P ratio of 10. Twenty-four hours after aerosol administration in pigs, lungs were excised and firefly luciferase activity was analyzed by bioluminescent imaging on lung tissue slices.

FIG. 3

Polyplexes of a branched 0.8/1 (ethylamine/propylamine units) copolymer ("br-Homo") and mRNA coding for firefly luciferase, and of branched polyethyleneimine ("br-PEI") and the mRNA were applied to mice as an intratracheal liquid and as an intratracheal spray. The figure shows the results of bioluminescence imaging tests using an IVIS Lumina XR Imaging System (Perkin Elmer, USA).

The invention claimed is:

1. A statistical copolymer comprising a plurality of repeating units (a) independently selected from repeating units of the following formulae (a1) and (a2):

$$—CH_2—CH_2—NH— \quad (a1)$$

$$—CH_2—CH_2—N{\diagup \atop \diagdown}, \quad (a2)$$

and a plurality of repeating units (b) independently selected from repeating units of the following formulae (b1) to (b4):

$$—CH_2—CH_2—CH_2—NH— \quad (b1)$$

$$—CH_2—CH_2—CH_2—N{\diagup \atop \diagdown} \quad (b2)$$

$$—CH_2—CH_2—CH_2—CH_2—NH— \quad (b3)$$

$$—CH_2—CH_2—CH_2—CH_2—N{\diagup \atop \diagdown} \quad (b4)$$

wherein the molar ratio of the sum of the repeating units (a) to the sum of the repeating units (b) lies within the range of 0.7/1.0 to 1.0/0.7, and wherein one or more of the nitrogen atoms of the repeating units (a) and/or (b) contained in the copolymer may be protonated to provide a cationic copolymer.

2. The copolymer of claim 1, which is a branched or dendritic copolymer comprising one or more types of repeating units selected from repeating units (a2), (b2) and (b4).

3. The copolymer of claim 1, which is a linear copolymer comprising repeating units (a1) and (b1).

4. The copolymer of claim 1, wherein the repeating units (a) and (b) account for 80 mol % or more of all repeating units in the copolymer.

5. The copolymer of claim 1, wherein repeating units (a) selected from (a1) and (a2) and repeating units (b) selected from (b1) and (b2) account for 80 mol % or more of all repeating units in the copolymer.

6. The copolymer of claim 1, wherein the terminal groups of the copolymer comprise one or more types of groups (c) independently selected from groups of the formulae (c1) to (c3):

$$—CH_2—CH_2—NH_2 \quad (c1)$$

$$—CH_2—CH_2—CH_2—NH_2 \quad (c2)$$

$$—CH_2—CH_2—CH_2—CH_2—NH_2 \quad (c3)$$

7. The copolymer of claim 1, wherein the molar ratio of the repeating units (a) to the repeating units (b) lies within the range of 0.8/1.0 to 1.0/0.8.

8. The copolymer of claim 1, which is obtainable by polymerizing a monomer mixture comprising aziridine, azetidine, and optionally pyrrolidine.

9. A composition comprising a nucleic acid and a copolymer in accordance with claim 1.

10. The composition of claim 9, wherein the nucleic acid is mRNA.

11. The composition of claim 9, wherein the copolymer is a cationic copolymer, and wherein the cationic copolymer forms a complex with the nucleic acid.

12. A pharmaceutical composition comprising a composition of claim 9, and a pharmaceutically acceptable carrier and/or diluent.

13. A method for delivering a nucleic acid to a target cell or tissue comprising the step of bringing a pharmaceutical composition of claim 12 into contact with the target cell or tissue, thereby delivering the nucleic acid to the target cell or tissue.

14. A method for delivering a nucleic acid to a target cell or tissue comprising the step of bringing a composition of claim 9 into contact with the target cell or tissue thereby delivering the nucleic acid to the target cell or tissue.

15. A method for the production of the copolymer of claim 1, comprising the step of polymerizing a monomer mixture comprising aziridine, azetidine and optionally pyrrolidine, thereby producing the copolymer, wherein the monomer mixture comprises a ratio of aziridine to azetidine and optionally pyrrolidione within the range of 0.7/1.0 to 1.0/0.7.

* * * * *